United States Patent [19]
Graessle et al.

[11] Patent Number: 5,565,634
[45] Date of Patent: Oct. 15, 1996

[54] ELECTRONIC TEST PACK USING PARAMETRIC MEASUREMENTS FOR STERLIZERS

[75] Inventors: Josef A. Graessle, Kaarst, Germany; Steven S. Kirckof, Oakdale, Calif.; Brian Kirk, Castle Donington, England; Werner R. Schwarz, Leverkusen; Theo N. Wildt, Titz, both of Germany

[73] Assignee: Minnesota Mining and Manufacturing Company, Saint Paul, Minn.

[21] Appl. No.: 584,713

[22] Filed: Jan. 11, 1996

Related U.S. Application Data

[63] Continuation of Ser. No. 250,052, May 27, 1994, abandoned.

[51] Int. Cl.$^6$ ........................................... G01M 3/16
[52] U.S. Cl. .................................. 73/865.9; 422/119
[58] Field of Search .................... 73/865.9; 374/142, 374/143; 116/216; 422/26, 28, 292, 298, 299, 119

[56] References Cited

U.S. PATENT DOCUMENTS

| | | | |
|---|---|---|---|
| 3,861,875 | 1/1975 | Joslyn | 422/119 |
| 3,982,893 | 9/1976 | Joslyn | 21/2 |
| 4,576,795 | 3/1986 | Bruso | 422/58 |
| 4,591,566 | 5/1986 | Smith | 435/291 |
| 4,850,716 | 7/1989 | Baker et al. | 374/160 |
| 4,865,814 | 9/1989 | Childress | 422/116 |
| 4,908,188 | 3/1990 | Jefferis, III et al. | 422/111 |
| 5,066,464 | 11/1991 | Augurt | 422/58 |
| 5,122,344 | 6/1992 | Schmoegner | 422/111 |
| 5,270,217 | 12/1993 | Dyke | 436/127 |

FOREIGN PATENT DOCUMENTS

| | | |
|---|---|---|
| 0155933 | 9/1985 | European Pat. Off. . |
| 0290929 | 11/1988 | European Pat. Off. . |
| 0419282 | 3/1991 | European Pat. Off. . |
| 0421760 | 4/1991 | European Pat. Off. .......... A61L 2/26 |
| 028245 | 5/1991 | European Pat. Off. .......... A61L 2/26 |
| 0604387 | 6/1994 | European Pat. Off. ........ G12B 17/06 |
| 1168184 | 7/1985 | U.S.S.R. . |
| WO93/18390 | 9/1963 | WIPO . |
| WO88/01372 | 2/1988 | WIPO ............................. G01M 3/16 |
| WO93/21964 | 11/1993 | WIPO ............................. A61L 2/00 |

OTHER PUBLICATIONS

Article by G. Hücker entitled "The Steriguard System: A New Measuring System for Batch Control in Steam Sterilisation"; Central Service Magazine; vol. 3, 1995, pp. 131–135.

Brochure entitled "The Bowie and Dick Test: Past, Present and Future", by Dr. I. Pankhania et al.; 3M Healthcare (1993).

"Steam Sterilization—The Response of the Test Pack" by R. Wichmann et al.; Biomedical Instrumentation & Technology, Sep./Oct. 1993; pp. 412–418.

Brochure entitled "Hospital Sterilisation HTM 2010 Study Day—Steam Quality in HTM 2010 and EN 285" by P. Hooper, 3M Healthcare; Nov. 4, 1993.

Brochure entitled "Hospital Sterilisation HTM 2010 Study Day—The Bowie and Dick test and its application in Health Technical Memorandum 2010" by B. Kirk, 3M Healthcare; Nov. 4, 1993.

*Primary Examiner*—Robert Raevis
*Attorney, Agent, or Firm*—Gary L. Griswold; Walter N. Kirn; Michael K. Ouyang

[57] ABSTRACT

A self-contained electronic test pack utilizes parametric measurments to determine the efficacy of a sterilization cycle. The electronic test pack is placed within a sterilization chamber and monitors and records environmental parameters at two predetermined locations during the sterilization cycle. More specifically, the test pack provides a challenging medium to challenge sterilant penetration to a first location and measures a first environmental condition at that location, and measures a second environmental condition within the sterilization chamber. The test pack records data associated with the first and second environmental conditions as well as time data from a timer within the test pack. The test pack may further process the data to determine whether adequate sterilant penetration has been achieved, or may transfer data to external devices to process the data.

69 Claims, 19 Drawing Sheets

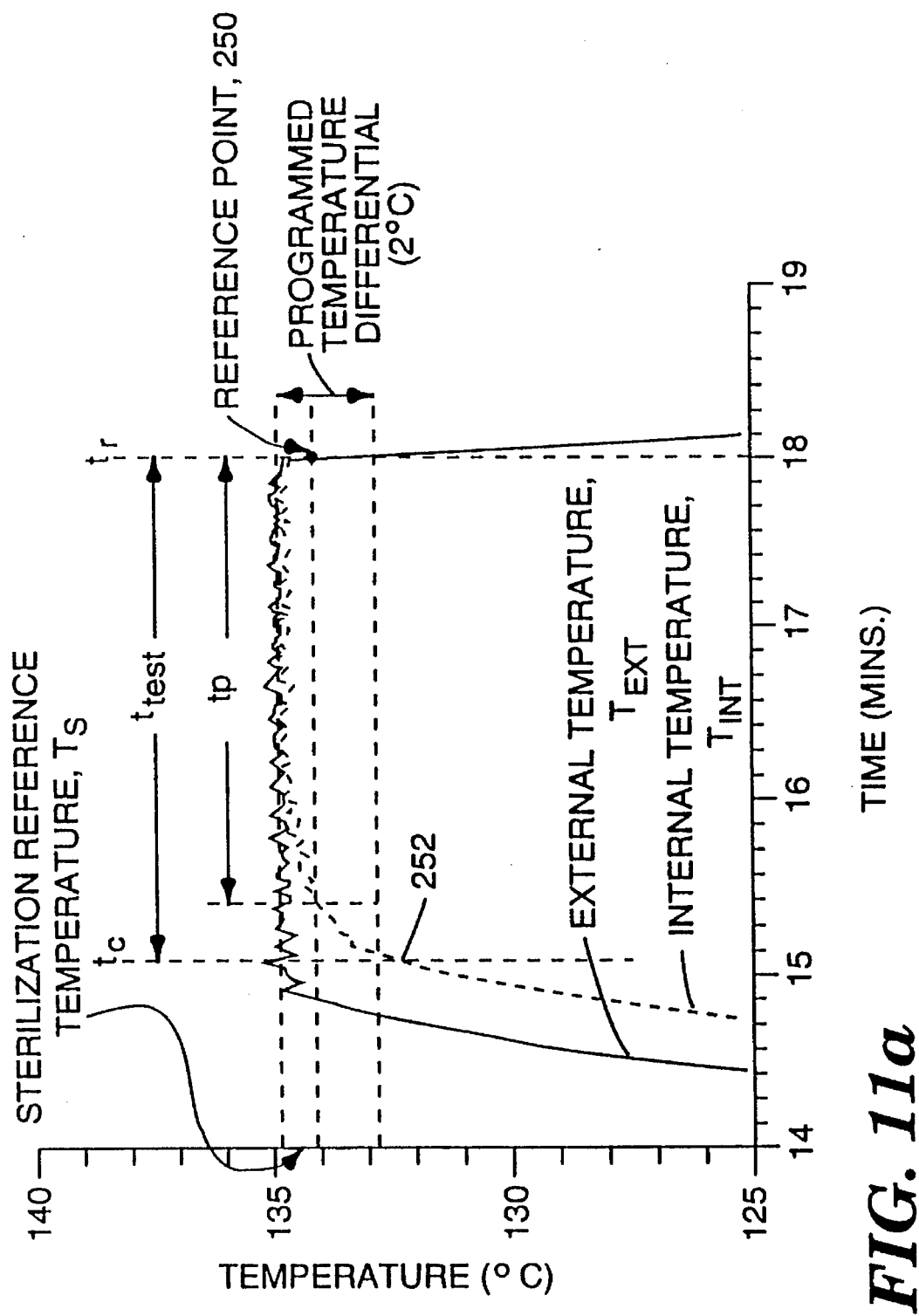

ELECTRONIC TEST PACK USING PARAMETRIC MEASUREMENTS FOR STERLIZERS

This is a continuation of application Ser. No. 08/250,052 filed May 27, 1994 (now abandoned)

FIELD OF THE INVENTION

The present invention relates generally to test packs and methods used to determine the efficacy of a sterilization cycle in sterilizers. More specifically, the present invention relates to test packs and methods that determine the efficacy of a sterilization cycle using parametric monitoring by an electronic test pack placed within the sterilization chamber.

BACKGROUND OF THE INVENTION

The steam sterilization process used to sterilize medical and hospital equipment cannot be effective unless the steam sterilant has been in contact with all surfaces of the materials being sterilized for the proper combination of time temperature, and steam quality. In porous load steam sterilizers, such as prevacuum steam sterilizers and gravity steam sterilizers, the process of sterilization is conducted in three main phases. In the first phase, air trapped within the porous materials being processed is removed. The second phase is a sterilizing stage, in which the load is subjected to steam under pressure for a recognized combination of time and temperature which are known to effect sterilization. The third phase is a drying phase in which condensation formed during the first two phases is removed by evacuating the chamber.

Air removal from the sterilization chamber may be achieved in a number of ways. For example, in a gravity steam sterilizer, the principle of gravity displacement is utilized, in which steam entering at the top gradually displaces the air through a valve in the base of the chamber. Alternatively, in a prevacuum steam sterilizer, air is removed forcibly by deep evacuation of the chamber or by a combination of evacuation and steam injection at either subatmospheric and/or superatmospheric pressures.

Any air which is not removed from the sterilizer during the air removal phase of the cycle or which leaks into the sterilizer during a subatmospheric pressure stage due to faulty gaskets, valves or seals, may form air pockets within any porous materials present. These air pockets will create a barrier to steam penetration, thereby preventing adequate sterilizing conditions being achieved for all surfaces of the materials being sterilized during the sterilizing phase. This is particularly true when porous materials such as hospital linens or fabrics are being sterilized since the air pockets prohibit the steam from reaching the interior layers of such materials. As a result, sterilization may not occur. Therefore, there is a need for an apparatus for determining the efficacy of sterilization cycles in sterilizers which operates by detecting whether there has been sufficient sterilant penetration.

One commonly used for procedure for evaluating the effectiveness of air removal during the air removal phase of a porous load sterilization cycle is known as the Bowie-Dick test. The typical Bowie-Dick test pack essentially consists of a stack of freshly laundered towels folded to a specific size. A chemical indicator sheet is then placed in the center of the pack. If the air removal within the sterilizer is insufficient, an air pocket will form in the center of the pack thereby preventing steam from contacting the steam sensitive chemical indicator sheet. The presence of the air pocket will be recorded by the failure of the indicator to undergo complete or uniform color change, indicative of adequate air removal. Although the Bowie-Dick type test is generally recognized as an adequate procedure for determining the efficacy of the air removal stage of prevacuum sterilizers, it stills presents many disadvantages. Since the test pack is not preassembled, it must be constructed every time the procedure is used to monitor sterilizer performance. The testing procedure may be somewhat inconsistent because varying factors, such as laundering, prehumidification, towel thickness and wear, and the number of towels used, alter the test results. Further, the preparation, assembly and use of the towel pack is time consuming and cumbersome. Therefore, alternative Bowie-Dick test packs have been developed to overcome these limitations.

An example of an alternative Bowie-Dick test pack is described in European Patent Application No. 90310367.9 to Hart et at. which describes a disposable test pack for steam or gas sterilizers. The Hart et at. test pack includes a container having top and bottom walls with a porous packing material disposed within the container. The packing material challenges the penetration of the sterilant by providing a restricted pathway which acts to impede the flow of the sterilant through the test pack. A removable lid seals the bottom end of the container, while a hole in the top wall of the container allows for the downward ingress of steam into the packing material within the container. The test pack includes a chemical indicator for detecting sterilant penetration. If sterilant successfully penetrates the packing material of the test pack, the chemical indicator sheet will undergo a complete color change. If the sterilant does not sufficiently penetrate the packing material, the chemical indicator will not undergo a complete uniform color change, thereby indicating inadequate air removal, or in other words, a Bowie-Dick test failure.

Parametric monitoring has been used to either monitor or control a sterilization cycle to ensure proper sterilization conditions are attained. For example, in U.S. Pat. No. 4,865,814 to Childress, an automatic sterilizer is disclosed which includes a microprocessor which monitors both the temperature and pressure levels inside the sterilization chamber and controls a heater to allow both pressure and temperature to reach predetermined levels before starting a timer. Once the timer is started, it is stopped if the pressure or temperature levels drop below a predetermined minimum. Sterilization criteria for steam sterilizers are often defined by requiring items to be sterilized to be subjected to a high quality steam at a given temperature for predetermined period of time. Since it is known that the pressure and temperature variables of saturated steam are dependent variables when saturated steam is enclosed in a sealed chamber, monitoring of these two variables can ensure that proper conditions are maintained during the sterilization cycle.

Although it is desirable to monitor environmental conditions within the sterilization chamber itself, it is even more desirable to be able to monitor the environmental conditions within or at the center of the actual load being sterilized. While external monitoring may be used, it is further desirable to have a self contained monitoring unit, which avoids having to introduce wires into the sterilization chamber, thereby potentially breaching the integrity of the chamber. In U.S. Pat. No. 3,982,893 to Joslyn discloses a system which includes a monitoring device which can be placed within a load to be sterilized. The device continuously monitors environmental conditions of the load, including at least humidity and temperature. The device generates a signal and transmits it to an antenna placed in the sterilization chamber which is wired to an outside device which controls the environmental parameters of the sterilizer. Thus, the Josyln device provides a self-contained device for controlling the operation of the sterilizer rather than testing the efficacy of the sterilization cycle by monitoring the humidity and temperature at the center of the load.

The devices used today to test the efficacy of sterilizers typically employ biological and/or chemical indicators. The Bowie-Dick test is an example of a chemical indicator test typically carried out at the start of testing each working day in order to determine the efficacy of the air removal stage of the cycle. The test is designed so detect the presence of residual air within the sterilization chamber due to leaks, failed gaskets or valves or the ingress of noncondensible gases present in the steam supply, all of which prevent adequate steam penetration into the porous mass constituting the test pack. Chemical indicator test sheets undergo a visible change from either one distinct color to another, for example, from an initial white to a final black color, upon exposure to the sterilization process. The consequence of inadequate steam penetration is a non-uniform color development across the surface of the chemical indicator test sheet. Chemical indicators, however, can be difficult to interpret, depending on the state of the color change.

Biological indicator systems provide information on the adequacy of the sterilization stage of the cycle. Biological indicator test systems employ living spores which are subjected to a sterilization cycle. After the cycle, the spores are incubated and the system detects if there is any growth. If there is no growth, it indicates that the sterilization process has been effective. Thus, biological indicators can determine whether conditions for sterilization were present, but the length of time to obtain results due to the incubation period is often at least 24 hours. Therefore, biological indicator systems are often used in conjunction with chemical indicators because the color change of the chemical indicators provides an instant result. Further, by using both chemical and biological indicators, information on both the adequacy of the air removal stage and the sterilization stage is provided.

Parametric monitoring has advantages over a chemical or biological indicator because results could be obtained instantaneously and the results can be in the form of a clear pass/fail decision. Moreover, rather than getting merely a pass/fail decision, detailed data is obtained which not only allow a pass/fail decision but also data can be obtained for allowing further analysis into the performance of the sterilizer. Therefore, what is desirable is a test pack which uses parametric measuring to determine if adequate sterilant penetration has been achieved within the test pack. More specifically, what is desirable is an alternative test pack which uses parametric measuring to determine the adequacy of the air removal stage of the sterilization cycle. What is more desirable is an alternative test pack which uses parametric measuring to not only determine the adequacy of the air removal stage but also the adequacy of the sterilization stage.

SUMMARY OF THE INVENTION

To overcome the limitations in the prior art described above, and to overcome other limitations that will become apparent upon reading and understanding the present specification, the present invention provides a system and method for determining the efficacy of a sterilization cycle using parametric measuring. An electronic test pack that is placed within a sterilization chamber monitors and records environmental parameters at two distinct locations. More specifically, the electronic test pack measures a first environmental condition at a location within the test pack, the location at the end of a challenging medium provided by the test pack. Thus, to reach the first location, sterilant must pass through the challenging medium. The test pack measures a second environmental condition at a predetermined location within the sterilization chamber. The test pack records data associated with the first and second environmental conditions, as well as time data from a timer within the test pack. The electronic test pack may further include a data processor to analyze the environmental conditions data and corresponding time data to determine whether adequate sterilant penetration has been achieved.

BRIEF DESCRIPTION OF THE DRAWINGS

The present invention will be more fully described with reference to the accompanying drawings wherein like reference numerals identify corresponding components, and:

FIGS. 11A and 11B are graphs of examples of a satisfactory and unsatisfactory sterilization cycle;

DETAILED DESCRIPTION OF A PREFERRED EMBODIMENT

To overcome the limitations in the prior art described above, and to overcome other limitations that will become apparent upon reading and understanding the present specification, the present invention provides a self-contained electronic test pack that determines the efficacy of a sterilization cycle by parametric monitoring. While the aforementioned systems used parametric monitoring to control the environmental parameters within the sterilization chamber to attempt to provide ideal environmental conditions for proper sterilization, the present invention monitors environmental conditions in at least two locations, typically at a chamber reference point and at a location within the load or simulated load. Then, using the measurements at both locations, combined with time data corresponding to the temperature measurements, the system can determine whether adequate sterilant penetration has been achieved.

Figure 1:
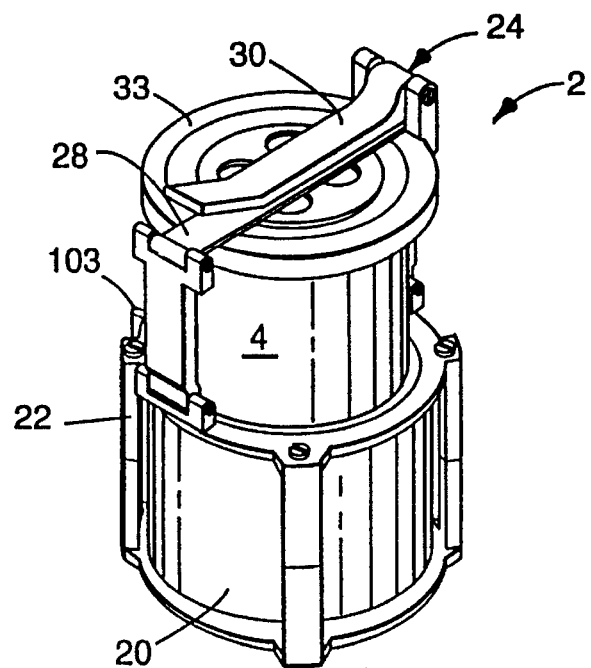
FIG. 1 is a perspective view of the electronic test pack of the present invention.
Figure 3:
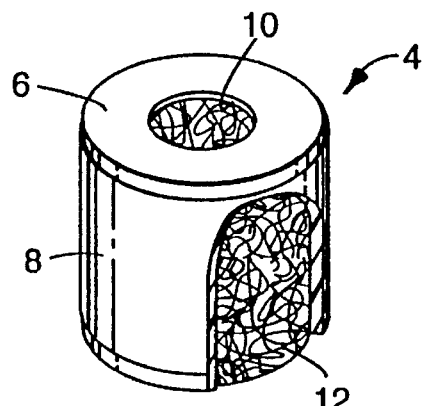
FIG. 3 is a perspective view of a container used for providing a challenging medium for sterilant, the container having a cut-out portion for showing the packing material within the container.
Figure 2:
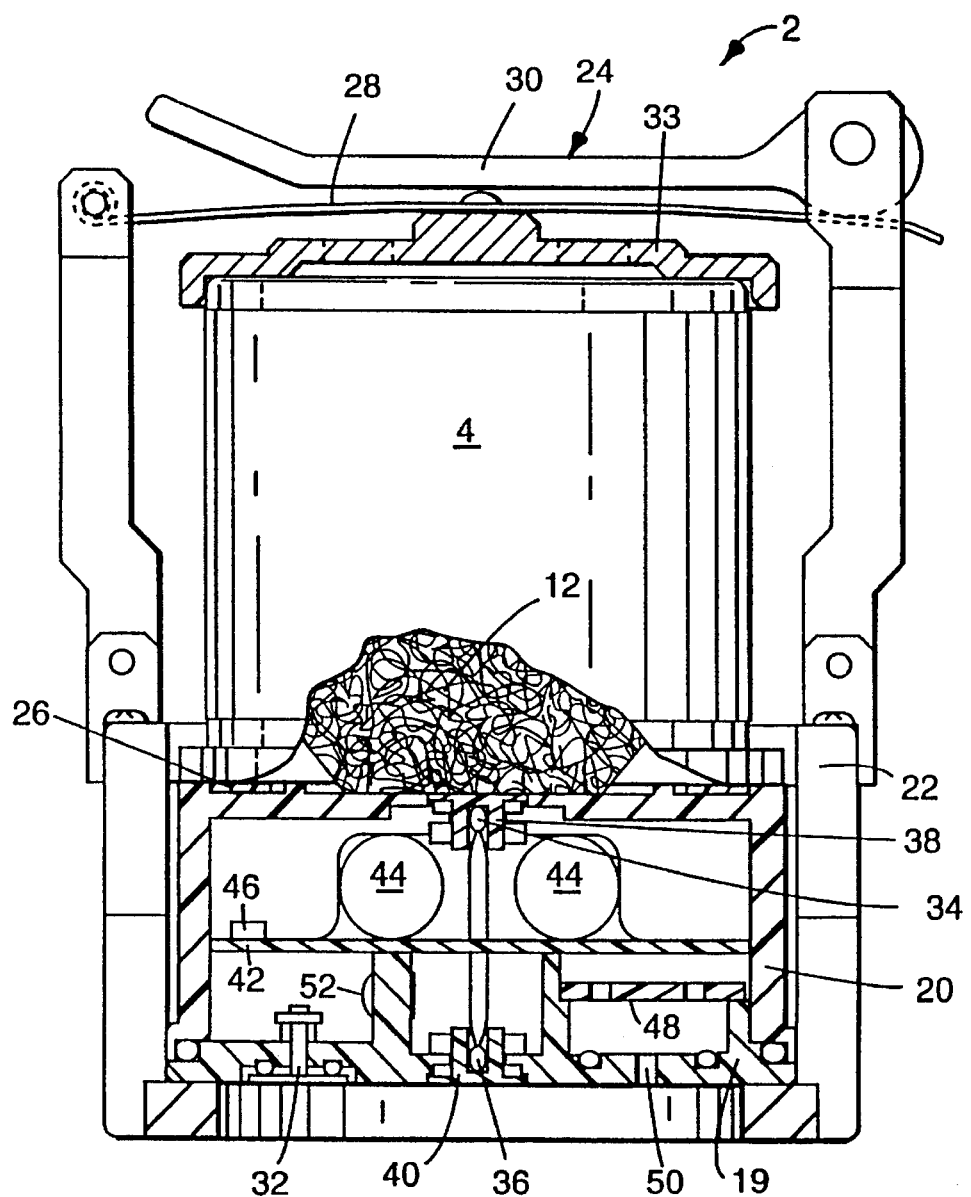
FIG. 2 is a cross-sectional view of the electronic test pack.

Referring to FIG. 1 and 2, a perspective and a cross-sectional view of self-contained electronic test pack 2 is shown. Container 4 is mounted on inner housing 20 and secured thereto by clamp 24. Outer housing 22 not only supports clamp 24 but also provides supporting structure for inner housing 20. FIG. 3 shows unmounted container 4, which is preferably is cylindrical in shape. Container 4 is made of gas and liquid-impermeable material, such as aluminum, although other materials, such as other metals, glass, film, metal laminated chip board, polypropylene, polyamides, polymethylpentenes, polyesters and polymethylmethacrylate may also be used. Container 4 has first end wall 6 and may include a second end wall opposite first end wall 6, although the second end wall is not required. Tubular sidewalls 8 extend between first end wall 6 and the second end Wall, or if no second end wall is used, is left open at the end opposite first end wall 6. Container 4 is preferably 5.8 cm. in height and 6.35 cm in diameter, and preferably has a volumetric capacity in the range of 2.54 $cm^3$ to 3,540 $cm^3$, more preferably in the range of 65.6 $cm^3$ to 1312 $cm^3$, and most preferably in the range of 114.8 $cm^3$ to 229.6 $cm^3$. First end wall 6 has at least one hole 10 having an area of between 0.0254 $cm^2$ and 7.62 $cm^2$ through it for the ingress of sterilant. Alternatively, the device may include larger numbers of holes 10, provided that the cumulative areas of the holes are between 0.019 $cm^2$ and 20.25 $cm^2$, preferably between 0.237 $cm^2$ and 5.06 $cm^2$.

Container 4 is at least partially filled with porous packing material 12 which challenges the penetration of the sterilant by defining a restricted pathway which impedes the flow of sterilant through container 4 during the sterilization cycle. Typically, packing material 12 is prepackaged in container 4. In another embodiment, packing material 12 is placed within container 4 prior to use and is retained therein by frictional forces between the inner surface of container 4 and the surface of challenging medium 12. Descriptions of some suitable fibrous materials for use as the challenging material and their properties are disclosed in commonly-assigned European Patent Application No. 90310367.9 to Hart et al., filed Sep. 21, 1990 and entitled "Disposable Test Packs for Steam or Gas Sterilizers," which is hereby incorporated by reference. Preferred fibrous packing materials are formed from polyolefin fibers, such as polyethylene, polypropylene, polybutylene, or copolymers of ethylene, polypropylene and/or butylene. A preferred fibrous packing material is comprised of compressed polypropylene blown microfiber. Another suitable packing material includes open cell porous foam materials made of polymers similar to the fibrous materials, including polyurethane or copolymers.

Figure 3A:
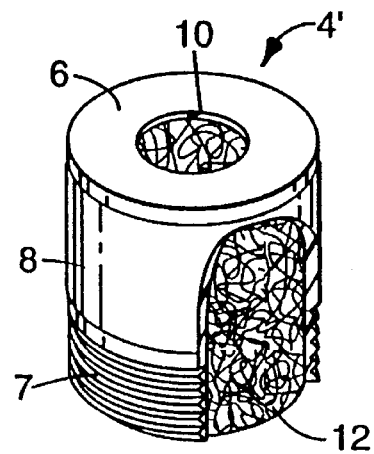
FIG. 3A is a perspective view of a threaded container used for providing a challenging medium for sterilant.
Figure 4A:
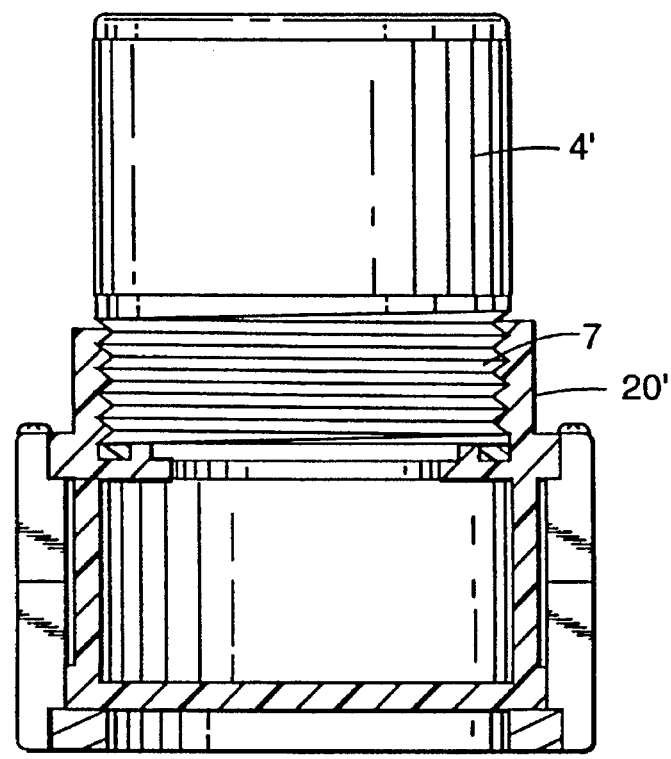
FIG. 4A is a cross-sectional view of a first embodiment of an electronic test pack, the first embodiment having a threaded container for providing a challenging medium.

Referring back to FIG. 2, outer housing 22 supports means for sealably mounting container 4 to inner housing 20. Inner housing 20 is positioned within outer housing 22. Clamp 24 is connected to outer housing 22 and is adapted to engage first wall 6, as shown in FIG. 3, of container 4 to apply downward pressure on container 4 such that the end of sidewall 8 opposite first wall 6 is embedded in seal 26. For example, lid 33 may be included to ensure clamp 24 provides uniform pressure along the circumference of first wall 6. If lid 33 is used, it must allow sterilant to freely reach hole 10 in container 4, such as by including at least one hole and preferably a plurality of holes. Seal 26 is preferably a circular O-ring made of any sealing material having a hardness of at least 40 shore and a temperature rating of over 150° C., such as silicone rubber. Clamp 24 preferably includes arm 28 and latch 30 for quick mounting of container 4, although any means for sealably and releasably mounting container 4 to inner housing may be used. For example, referring to FIG. 3A, container 4' may include threaded portion 7 or may includes a bayonet fitting, such that it will sealably fix onto inner housing 20' as shown in FIG. 4A. In FIG. 4A, inner housing 20' extends to receive threaded portion 7 of container 4'. The height of packing material 12 is slightly larger than the length of container 4' such that when container 4' is fixed into place, a slight compressive force is applied to packing material 12, thereby forming a seal with inner housing 20'. Referring back to FIG. 2, inner housing 20 includes a removable bottom wall 19, which may be removed when changing batteries or recalibrating the test pack. In such an embodiment where inner housing 20 includes removable bottom wall 19, outer housing 22 secures bottom wall 19 such that inner housing 20 is sealed. Outer housing 22 is constructed of a structurally rigid material, such that when stressed, it returns to its original shape. For example, any type of metal, as well as glass fiber or carbon fiber reinforced plastic with softening temperatures higher than 150° C. can be used for outer housing 22. In the embodiment shown in FIG. 1, outer housing 22 further provides a base for clamps 24.

Figure 4B:
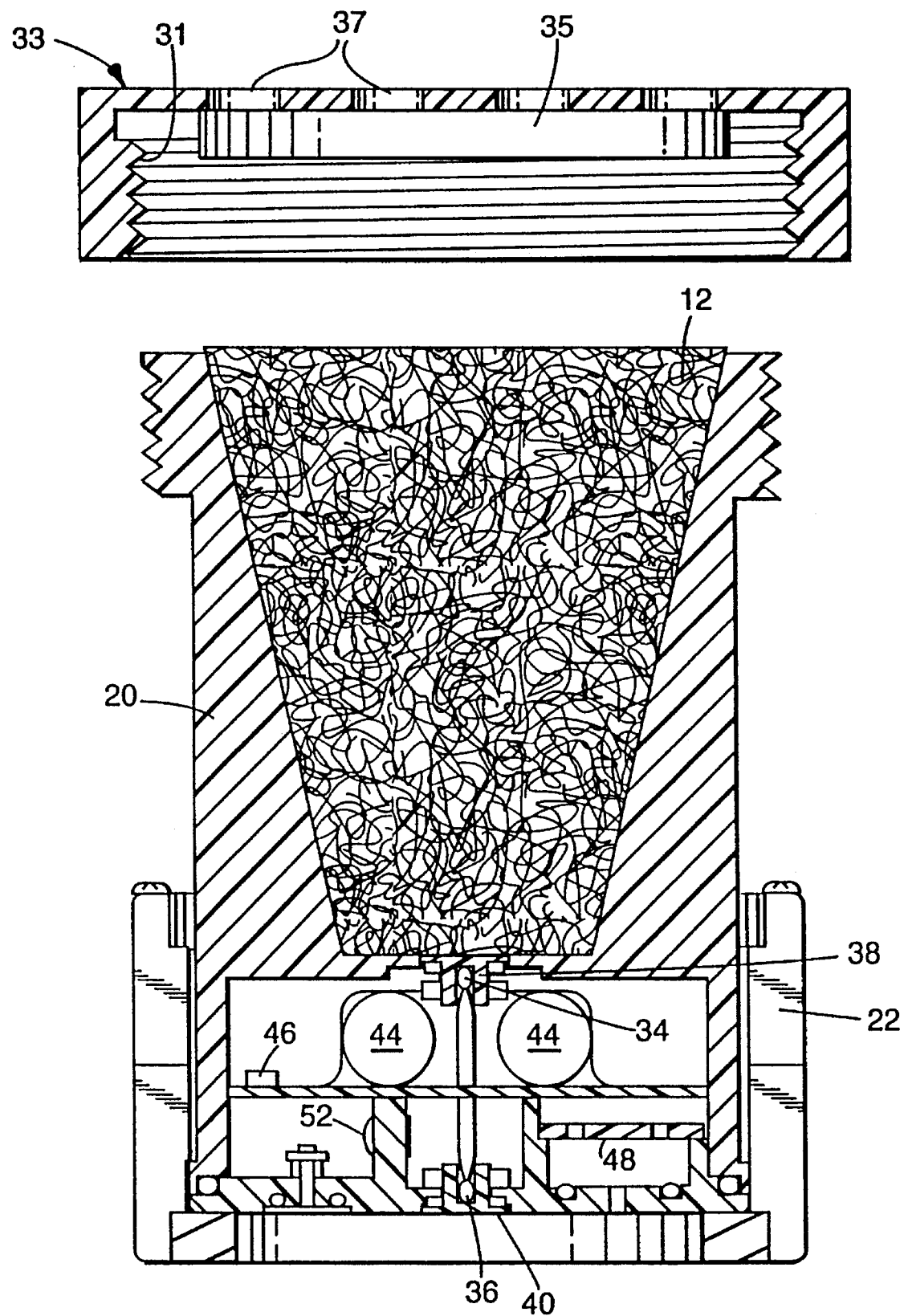
FIG. 4B is a cross-sectional view of a second embodiment of an electronic test pack, the second embodiment having a conical-shaped foam challenging medium.

Referring to FIGS. 4B, a second embodiment of the electronic test pack of the present invention is shown. Inner housing 20 extends to also house packing material 12. Packing material 12, for example, a plug of polyurethane open cell foam, provides a challenging medium and is placed within inner housing 20. Foam plug 12 which may be either reusable or disposable may be cylindrical or conical, as shown in FIG. 4B, in shape. In the case of a cylindrical plug, the diameter of the plug may vary between the diameter of cap 38 and the diameter of inner housing 20. In the case of a conical plug, the diameter of the end of the plug abutting cap 38 will be no smaller than the diameter of cap 38. The diameter of the other end of the plug will be larger than the diameter of the end abutting cap 38 and smaller than the diameter of inner housing, and is preferably in the range of 2 to 15 cm. The height of plug 12 is preferably in the range of 3 to 30 cm. Lid 33 includes at least one hole and preferably a plurality of holes 37 for the ingress of sterilant. Lid 33 further includes a suitable attaching and sealing means such as a threaded portion 31 or a bayonet fitting. Lid 33 is designed to apply a downward force on plug 12, such as including downward depending portion 35, to radially expand foam plug 12, thereby forming a seal against the inner walls of inner housing 20. Alternatively, packing material 12 is placed within inner housing 20 prior to use and retained therein by frictional forces between the inner surface of inner housing 20 and the surface of packing material 12. In such an embodiment, lid 33 is not necessary.

Figure 4C:
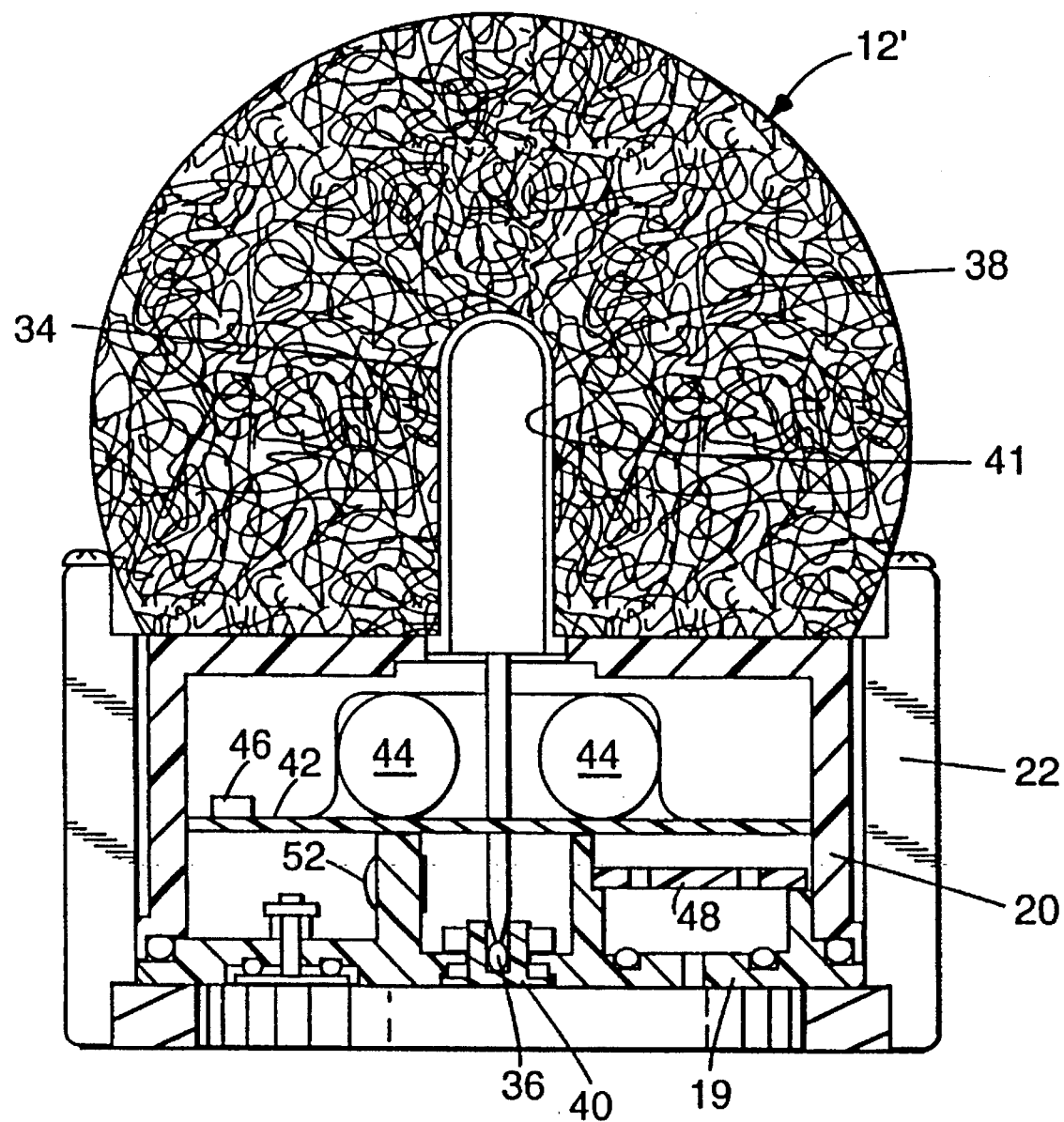
FIG. 4C is a cross-sectional view of a third embodiment of an electronic test pack, the third embodiment having a spherical-shaped foam challenging medium.

Referring to FIG. 4C, a third embodiment of the present invention is shown. In this embodiment, cap 38 protrudes from inner housing 20 to allow temperature sensor 34 to measure temperatures a predetermined distance from inner housing 20. Challenging medium 12', for example, a plug of open cell polyurethane foam, is placed over cap 38. Challenging medium 12', which may be either disposable or reusable, is preferably spherical or cubic, although any suitable three dimensional geometric shape may be employed. In the case of a spherical plug, the diameter will be in the range of 2 to 15 cm. In the case of a cubic plug, each side will be in the range of 2 to 15 cm. Bore 41 has a diameter of approximately 15% less than the diameter of cap 38 such that when challenging medium 12' is placed over cap 38, a tight seal is formed. Further, the portion of challenging medium 12' in contact with inner housing 20 could further be sealed by including a pressure sensitive adhesive. Bore 41 of spherical challenging medium 12' has a length such that temperature sensor 34 measures the temperature at the geometric center of challenging medium 12'.

Referring back to FIG. 2, inner housing 20 is preferably cylindrical in shape and is constructed of a transparent, rigid material having broad temperature stability such that inner housing 20 does not warp or change dimensions when exposed to a broad range of temperatures. A preferred material for inner housing 20 is Ultrason E, a polysulfone plastic. Inner housing is approximately 4 cm high and 5 cm in diameter. The contents housed inside inner housing 20 may be protected from the extreme heat within the sterilization chamber by a vacuum within inner housing 20. A internal vacuum prevents air from conducting heat from the inner walls of inner housing 20 to the components housed within inner housing 20. In one embodiment, inner housing 20 is evacuated when it is assembled. Inner housing 20 is then sealed to preferably hold the pressure within inner housing 20 under 0.2 Bars absolute pressure. In another embodiment, inner housing 20 includes one-way valve 32. Valve 32 opens when the pressure external to inner housing 20 falls below a predetermined value, as determined by the spring tension of valve 32 and the air pressure outside of valve 32. When test pack 2 includes one-way valve 32, it is not necessary to pull a vacuum when inner housing 20 is assembled. If no vacuum is pulled at assembly, when a vacuum is pulled within a sterilization chamber with test pack 2 placed inside, valve 32 opens to allow a vacuum also to be pulled within inner housing 20. If a vacuum was pulled at assembly, valve 32 opens to allow a deeper vacuum to be pulled if the pressure within the sterilization chamber falls below the pressure within inner housing 20.

Inner housing 20 houses the electronics and sensors of electronic test pack 2. Temperature sensors 34 and 36 may be any of a number of temperature transducers, such as thermocouples or thermistors. Temperature sensors 34 and 36 may be protected from the external environment, such as by caps 38 and 40. Cap 38 may be constructed of any suitable thermally conductive material, such as stainless steel or aluminum. Caps 38 and 40 further facilitate the seating of sensors 34 and 36 within inner housing 20. Temperature sensor 34 is positioned such that it measures the temperature at a location at the end of a challenging path, such that sterilant must penetrate through the packing material to reach the sensor location. In FIG. 2, sterilant would have to penetrate through the packing material within container 4 to reach temperature sensor 34. Temperature sensor 40, on the other hand, measures the external temperature. Thus, when electronic test pack 2 is placed within a sterilization chamber, temperature sensor 40 measures the chamber temperature.

Figure 5:
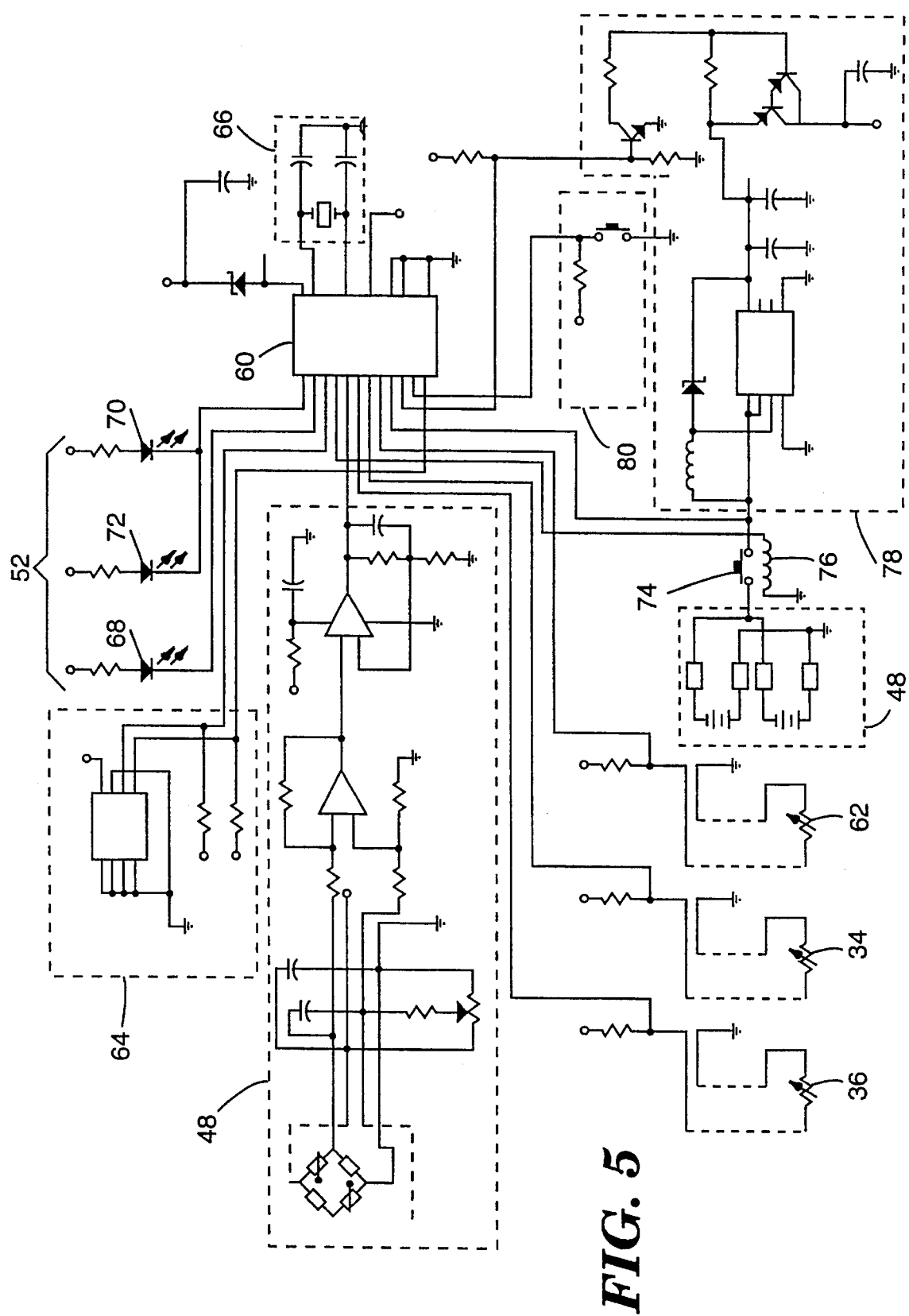
FIG. 5 is a circuit diagrams of a circuit within the test pack.

Circuit board 42 is thermally isolated from the walls of inner housing 20 to prevent conduction of external heat to the electronics mounted on the board. Surface mounted chips 46, batteries 44, temperature sensors 34 and 36, light emitting diode 52 and pressure sensor 48 all may be electrically connected to circuit board 42. Referring to FIG. 5, a circuit diagram is shown of a preferred circuit for electronic test pack 2. Temperature sensors 34 and 36 measure the temperatures within the test pack and within the sterilization chamber, respectively. Temperature sensor 62 measures the temperature at circuit board 42 to determine if the temperature exceeds the operating temperature of the circuit components. If microprocessor 60 determines that the temperature sensed at sensor 62 exceeds the operating temperature, microprocessor 60 shuts off the circuit. Temperature sensor 62 is a safety measure to protect the circuit components. Circuit components, particularly if following military standards, are rated to safely operate in ambient temperatures up to a prescribed minimum, such as 125° C. The same circuit components usually have a higher storage temperature than working temperature, such as a storage temperature of 150° C. Thus, if circuit components are rated for an ambient temperature of 125° C., microprocessor 60 will shut off the circuit if sensor 62 senses a temperature that exceeds 125° C., thereby protecting the circuit components up to a temperature of 150° C. Circuit board 42 further may include other sensors, such as relative humidity sensors, conductivity sensors, or pressure sensors. Referring to FIGS. 2 and 5, pressure sensor 48 is electrically connected to circuit board 42. Inner housing 20 includes hole 50 to allow the sterilization chamber pressure to be sensed by pressure sensor 48. Hole 50 and the measuring surface of pressure sensor 48 are isolated from the environment within housing 20. Circuit board 42 also may include its own batteries 44, ON/OFF switch, including magnetically actuated bi-stable switch 74 and inductive coil 76, and switched power supply 78.

As temperature sensors 34 and 36 measure temperatures, the temperature readings are stored in memory 64. In a preferred embodiment, memory 64 is an electrically erasable programmable read-only memory (EEPROM). As temperatures are stored in memory 64, crystal controlled frequency base 66 provides a timing base for microprocessor. Microprocessor 60 converts the pulses from crystal 66 to time data that corresponds to the temperature data. Time data is also stored in memory 64. In one embodiment, once microprocessor 60 determines that a sterilization cycle is complete, it then determines whether the sterilization cycle is satisfactory, in other words, that the sterilant has penetrated through the packing material in container 4. If microprocessor 60 determines that the sterilization cycle was satisfactory, light emitting diode (LED) 68 emits light. In a completely self-contained electronic test pack, only a single LED is necessary to indicate whether the cycle has passed. With a single LED, the LED may continuously burn to indicate a pass cycle and may flash to indicate a fail cycle. In one embodiment of a self-contained test pack, two LEDs are included to indicate a pass cycle and fail cycle. If the sterilization cycle passed, LED 68 emits a green light. If microprocessor 60 determines that the sterilization cycle failed, LED 70 emits a red light. In another embodiment, LED 68 would emit a continuous green light while LED 70 would emit a flashing red light. In yet another embodiment of a self contained electronic test pack, a plurality of LEDs are included to indicate a pass or a fail cycle, and in the case of a fail cycle, the magnitude of the level of failure. If the sterilization cycle passes, LED 68 emits a continuous green light. If microprocessor 60 determines that the cycle fails, it determines the level of failure and causes an appopriate number of LEDs to emit flashing red light.

Figure 6:
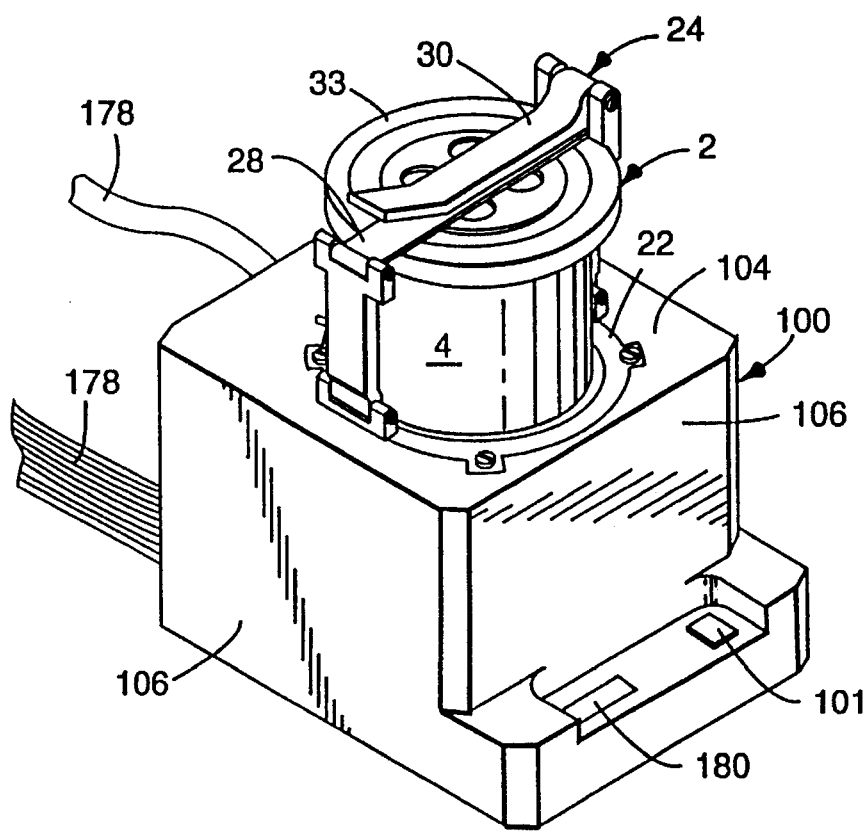
FIG. 6 is a perspective view of a electronic test pack placed within a stand.
Figure 6A:
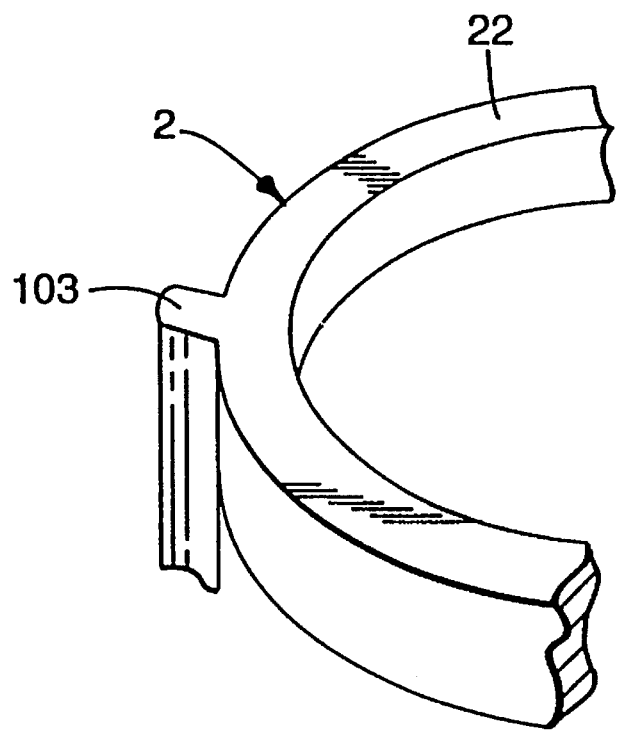
FIG. 6A is an exploded view of a breakaway portion of the electronic test pack and the stand, showing the predetermined orientation with which the test pack can be placed into the stand.
Figure 6A:
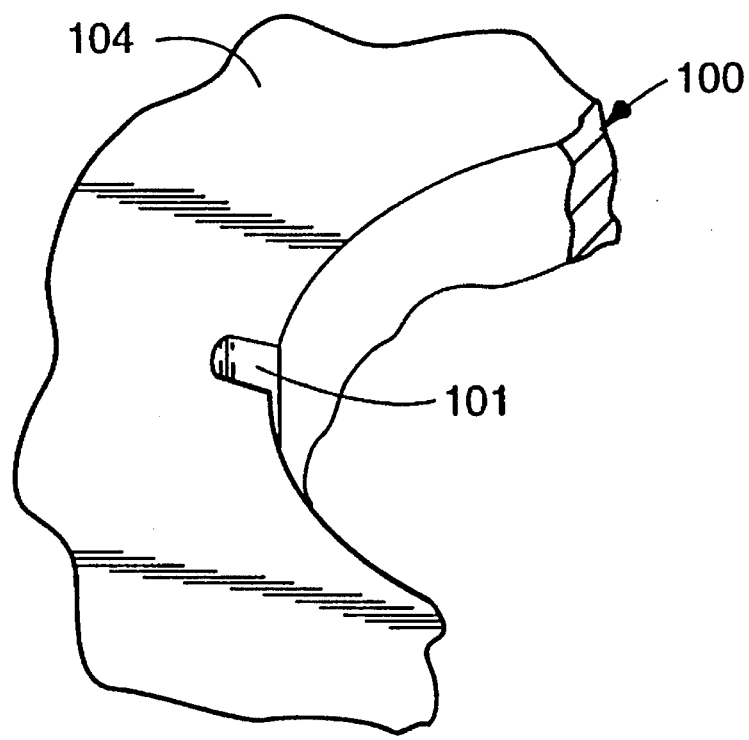
Figure 7:
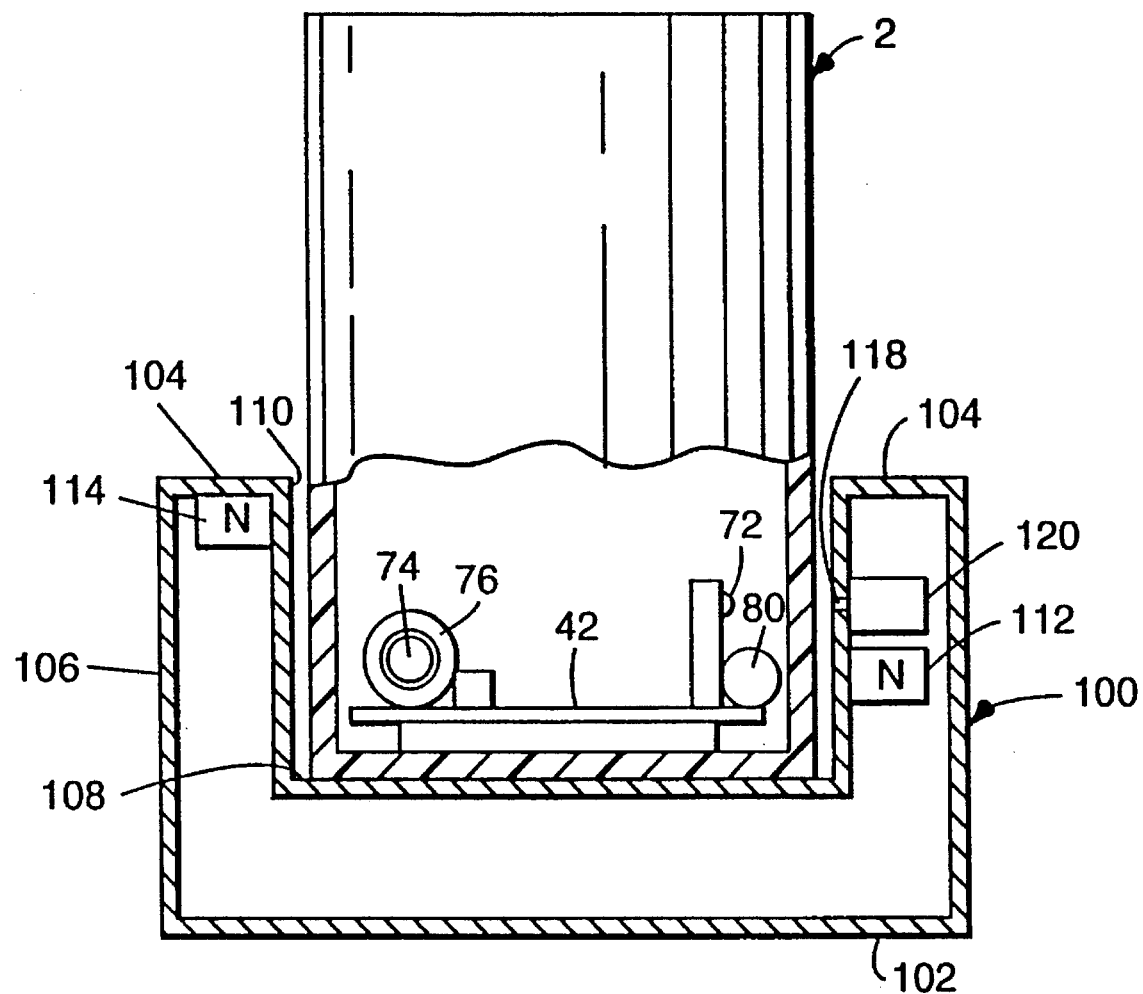
FIG. 7 is a cross-sectional view of an electronic test pack within a stand.

In some situations, however, it is desirable to transfer the data stored in memory 64 to an outside processor or memory. Data transfer may be initiated by actuating magnetically actuated switch 80, preferably a Reed switch, and ON/OFF switch 74. Data is then transferred optically using LED 72. Referring to FIGS. 6 and 7, a preferred device for turning on the power of the electronic test pack and for data transfer will now be described. Because electronic test pack 2 is placed in extreme environmental conditions, it is desirable to have the power and data switches completely within inner housing 20, and even more desirable to have the switches thermally isolated from the external temperature. Also, it is desirable for the power switch to automatically turn off when the test pack is not in use. Therefore, in a preferred embodiment of the present invention, proximity switching is used to turn on the power of the electronic test pack and to initiate both data transfer. Data transfer and power switching stand 100 preferably includes outer bottom wall 102, top wall portion 104 and outer sidewalls 106 extending therebetween. Stand 100 further includes inner bottom wall 108 and inner sidewalls 110 extending between top wall portion 104 and inner bottom wall 108. Stand 100 may be constructed of any non-magnetic material such as a plastic or aluminum. Inner bottom wall 108 and inner sidewall 110 are configured to allow electronic test pack 2 to be placed within stand 100 in a predetermined orientation. The predetermined orientation is based on the locations of data transfer switch 80 used for initiating data transfer, ON/OFF switch 74 and data transmission LED 72. Data transfer switch 80 and ON/OFF switch 74 are preferably mounted on opposite ends of circuit board 42. Stand 104 is adapted to receive electronic test pack 2 such that data transfer switch 80 and ON/OFF switch 74 pass data transfer magnet 112 and power magnet 114, respectively. For example, referring to FIG. 6A, stand 100 includes longitudinal notch 101 extending between top wall portion 104 and inner bottom wall 108, not shown. Outer housing 22 of test pack 2 includes longitudinal ridge 103, sized to slidably engage notch 101. Because ridge 103 protrudes from outer housing 22, the only orientation that test pack 2 can be placed into stand 100 is by aligning ridge 103 with notch 101, and therefore the magnets and switches may be placed accordingly. Data transfer magnet 112 and power magnet 114 may either be permanent magnets positioned within stand 100 or they may be user energized inductive coils for selective initiation of data transfer or turning on the power, for example, by depressing button 101 on stand 100. The magnets must radiate a magnetic field that is strong enough to actuate its corresponding switch within the test pack, but not so strong as to actuate the other switch. For example, the magnetic field from power magnet 114 must be strong enough such that when test pack 2 is placed in stand 100, ON/OFF switch 74 will pass through the field but data transfer switch 80 will not. In one embodiment, a field strength of 1400 Gauss is used. In such an embodiment, the distance from the switches to the magnets is preferably between 20 to 30 mm. Numerous combinations of actuating components 112 and 114 and sensing components 74 and 80 can be used in place of the magnetic actuators and Reed switches. Some examples of proximity switching configurations include using a magnetic actuator and a Hall-effect device, a magnetic actuator and a magneto-resistive device, a light emitting diode (LED) light source and an optical switch, a magneto-dynamic transformer, electrostatic capacitive coupling, and electrodynamic capacitive coupling.

In a preferred embodiment, the electronic test pack is capable of transferring stored data to outside hardware, such as a memory device, a computer or a printer. Data transfer switch 80 is a magnetically actuated switching device having a stable open state, when switch 80 is not proximate to a magnetic field of a predetermined strength, and a closed state, when switch 80 is in a magnetic field of the predetermined strength. Preferably, the magnetic field required to keep switch 80 closed should be a minimum of 10 Gauss. When ON/OFF switch 74 has been actuated and data transfer switch 80 is closed within a predetermined time, such as 10 seconds, it signals microprocessor 60 to initiate data transfer, transferring all data stored within memory 64 to external hardware. In a preferred embodiment, data transfer is accomplished using infrared light emitting diode (IR LED) 72 mounted on circuit board 42 and infrared sensor 120 located within stand 100. An infrared diode and sensor is preferable because surrounding visible light will not affect the data transfer. Examples of LEDs and sensors used for data transmission are SE2470-2 and SDP8602-3, manufactured by Honeywell, Inc. of Minneapolis, Minn. Stand 104 includes an aperture in inner sidewall 110 such that light emitted from IR LED 72 can be sensed by sensor 120. IR LED 72 transfers data in a binary stream, using infrared light pulses, preferably in an RS-232 data format. Stand 100 further includes interfaces 178 to connect to external devices.

Figure 8:
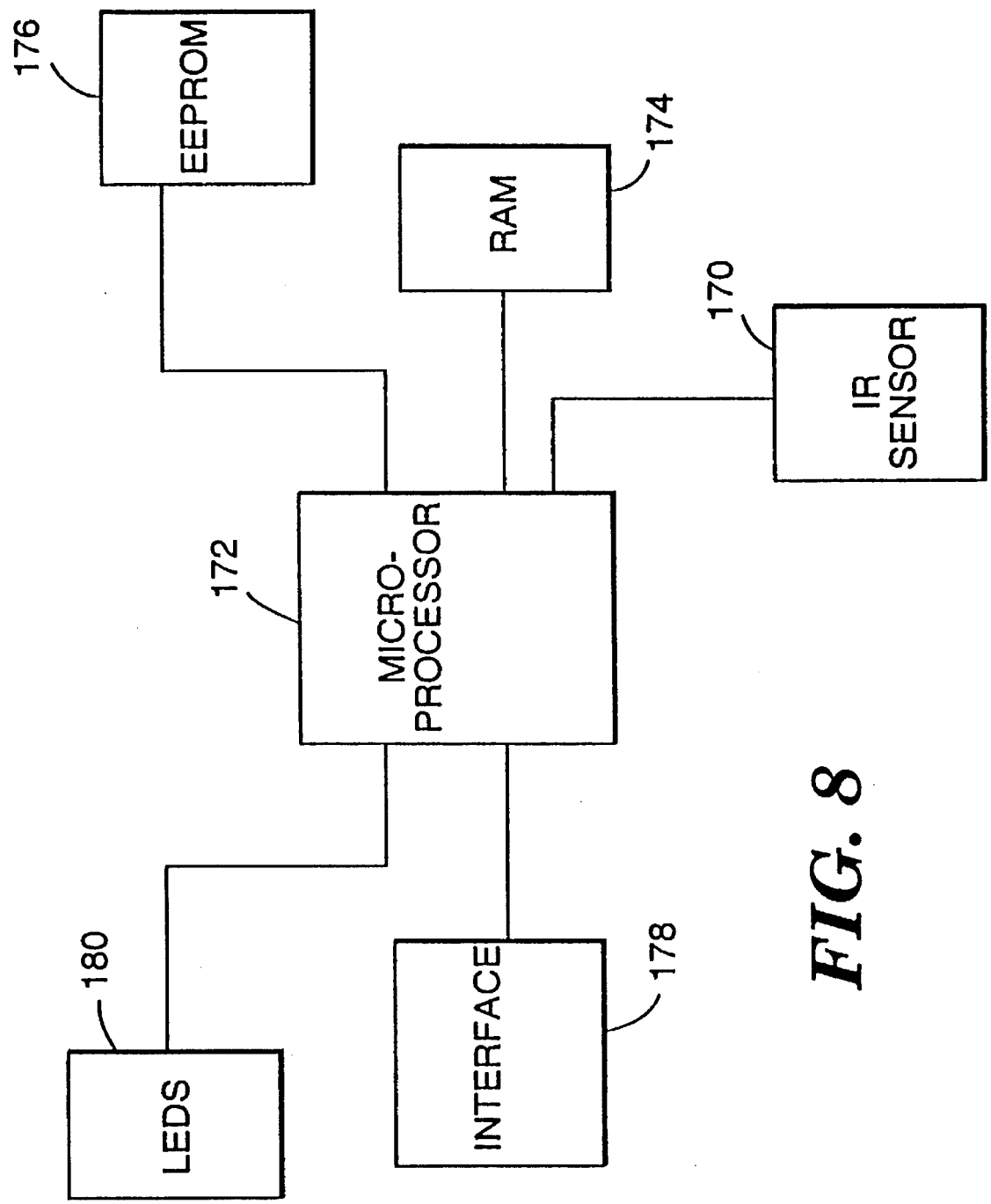
FIG. 8 is a block diagram of a circuit within the stand.

Referring to FIG. 8, a block diagram is shown for a preferred circuit for receiving and processing data from the electronic test pack. Infrared sensor 170 receives light pulses from IR LED 72 and microprocessor 172 stores the. data in random access memory (RAM) 174. If evaluation of the efficacy of the sterilization cycle was not performed by the microprocessor on the circuit board within the electronic test pack, microprocessor 172 can perform the evaluation. Stand 100 may further include LEDs, LED bar 180, or some other appropriate display to indicate whether the sterilization cycle passed or failed. Stand 100 may also include interfaces 178 to a personal computer for more sophisticated evaluation, to a memory device to store the data, or to a printer to print out data and results of the evaluations.

ON/OFF switch 74 is a bi-stable magnetically actuated switching device, such as a bi-stable Reed switch. ON/OFF switch 74 is switched from an OFF position to an ON position when test pack 2 is inserted into or taken out of stand 100 in the predetermined orientation and switch 74 passes through the magnetic field of power magnet 114. Switch 74 remains in the stable ON position until a magnetic field of opposite polarity is placed proximate to switch 74, thereby switching switch 74 to a second stable state, an OFF position. In a preferred embodiment, inductive coil 76 is mounted on circuit board 42 proximate to switch 74, and even more preferably switch 74 is mounted in the center of coil 76. Inductive coil 76 generates a magnetic field of opposite polarity and of sufficient strength to switch ON/OFF switch 74 to the OFF position. When switch 74 is at the ON position, microprocessor 60 determines when to energize coil 76, thereby turning the power of electronic test pack 2 off.

Figure 9:
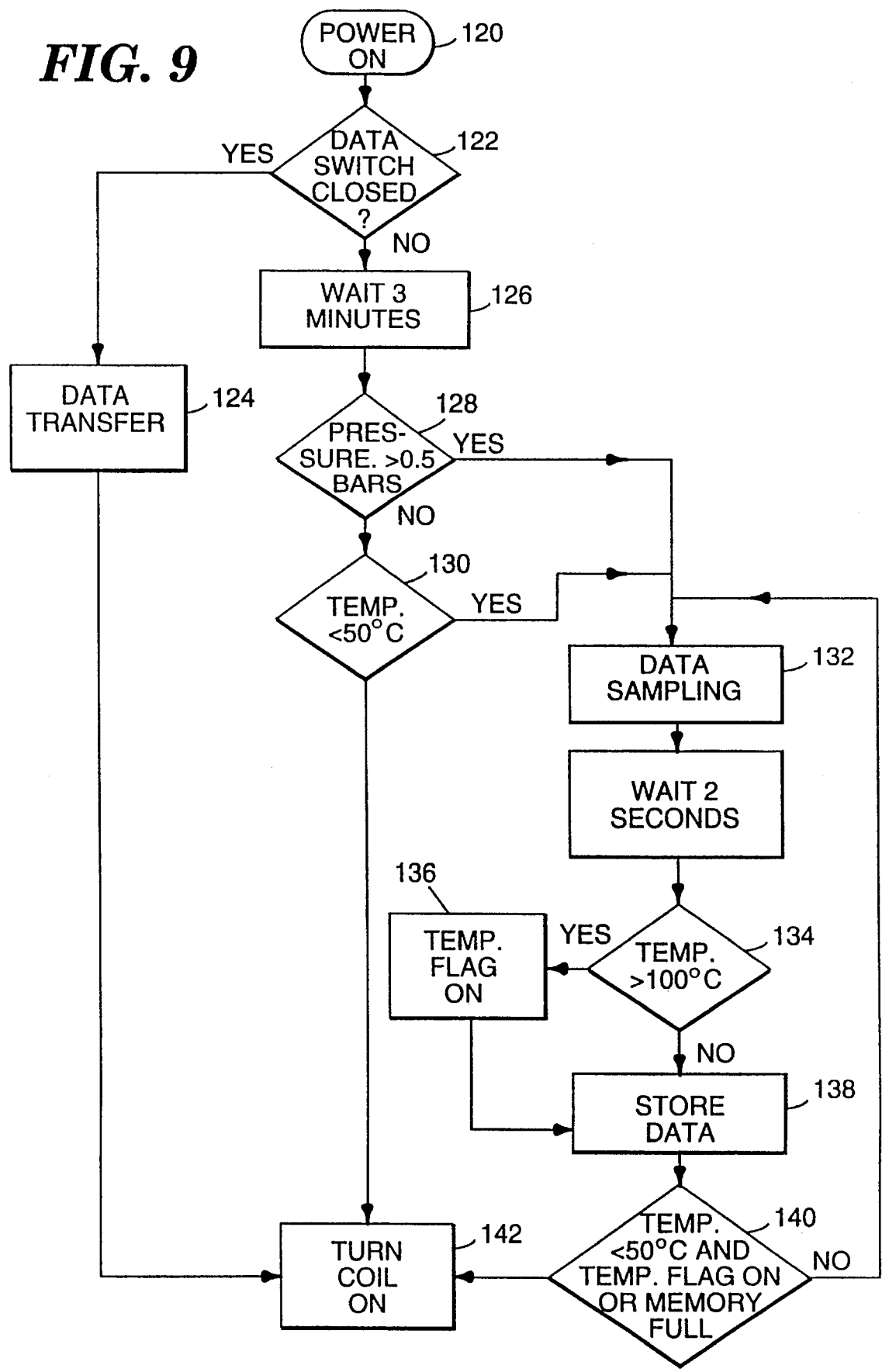
FIG. 9 is a flow diagram for energizing an inductive coil, thereby turning off the power of the electronic test pack.

Referring to FIG. 9, a preferred flow diagram for determining when to energize inductive coil 76, thereby turning the power of the test pack off is shown. Once power switch 74 is turned on, microprocessor 60 will energize inductive coil 76 at block 142 if any of three possible conditions are satisfied. A first condition for turning off the power of the electronic test pack is if data transfer is complete as shown in block 124. In one embodiment, the electronic test pack is capable of transferring stored data to outside hardware. Once power is on, if the data switch is closed, then data transfer is initiated. When test pack 2 is placed within stand 140 for data transfer, microprocessor 60 reads memory 64 and transfers data through LED 72. When data transfer is complete, microprocessor energizes coil 76. If the data transfer switch is not closed, the electronic test pack is then in a data collection mode. A second condition for turning off the power of the electronic test pack is if microprocessor 60 determines that the test pack has not been placed in a sterilization chamber, and thus data collection is not necessary. Any of a number of parameters can be measured to make this determination. In one embodiment, microprocessor 60 evaluates chamber pressure and temperature measurements after a predetermined time. Microprocessor then determines whether the measurements are consistent with a chamber pressure and temperature after a sterilization cycle has begun. At blocks 126, 128, and 130, microprocessor 60 determines whether the chamber temperature is less than 50° C. or the chamber pressure is lower than 0.5 Bars three minutes after the test pack has been turned on. If either condition is satisfied, microprocessor 60 energizes coil 76, thereby turning off the test pack. In another embodiment, microprocessor 60 examines temperature and pressure data three minutes after initiation of data collection and compares it with initial readings. If the temperature and pressure data three minutes after initation of data collection is less than ±10% different from the initial readings, microprocessor 60 energizes coil 76. A third condition for turning off the test pack is completion of a sterilization cycle. At block 132, microprocessor 60 has determined that the electronic test pack has been placed within a sterilization chamber and data collection should commence. The collected data is stored at block 138. While collecting data, microprocessor 60 also tracks the chamber temperature. When the chamber temperature exceeds 100° C. at block 134, microprocessor 60 determines that the test pack is being subjected to a sterilization cycle and sets temperature flag at block 136. Once the threshold temperature of 100° C. has been achieved, microprocessor 60 continues to track the chamber temperature to determine if the sterilization cycle has been completed. When the chamber temperature lowers to a second threshold temperature, such as 50° C. at block 140, microprocessor 60 energizes inductive coil 76 at block 142. Inductive coil 76 emits a magnetic pulse which opens switch 74, thereby turning switch 74 to the OFF position. Microprocessor 60 will also energize coil 76 if memory 64 is full.

Figure 9A:
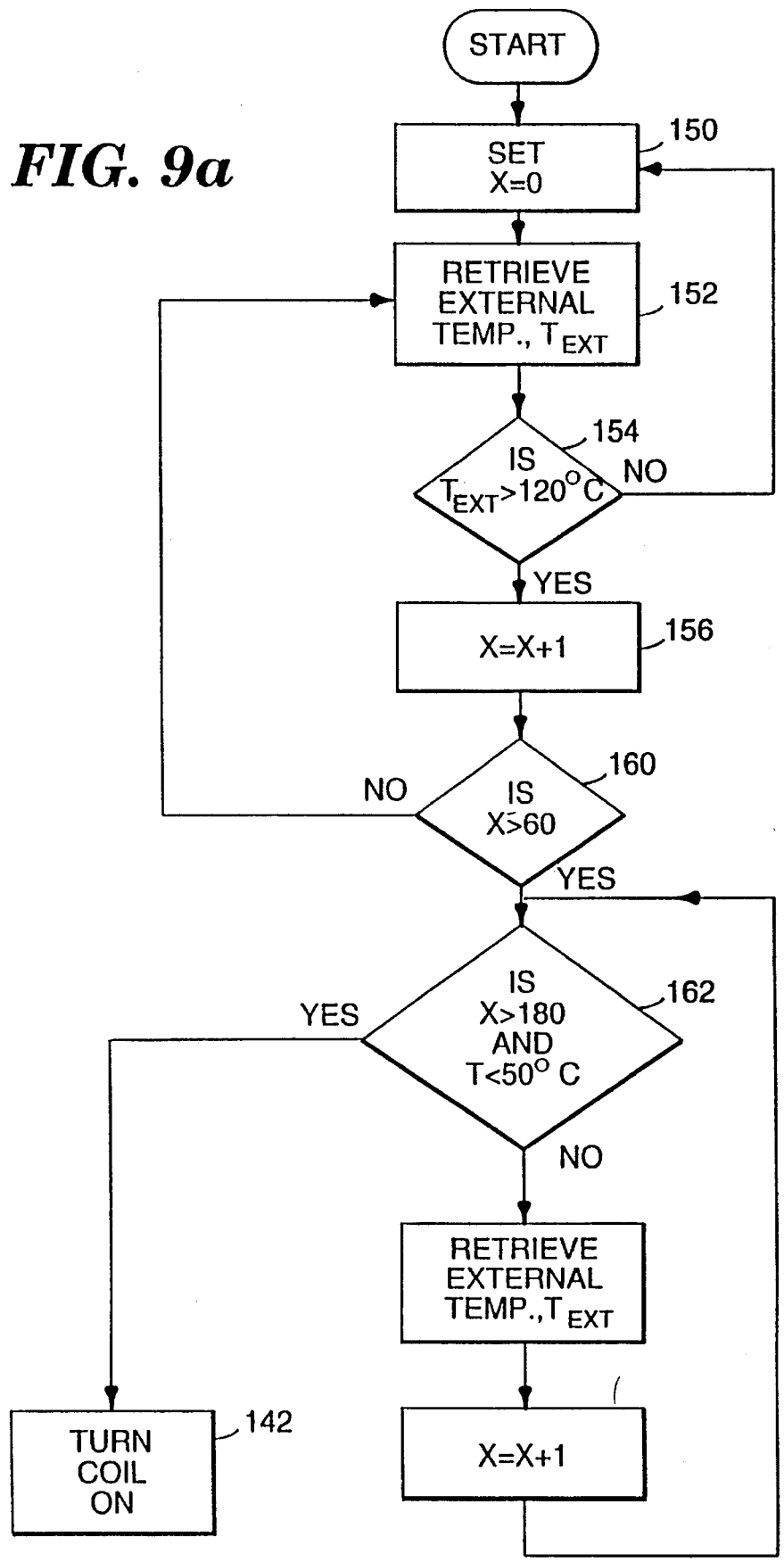
FIG. 9A is a flow diagram for determining whether a sterilization cycle has been completed.

Referring to FIG. 9A, a block diagram of another software program for turning off the test pack after a sterilization cycle is completed is shown. A counter is initialized to zero at block 150. At blocks 152 and 154, the sterilization chamber temperature $T_{EXT}$ is retrieved from the external temperature sensor and compared with a predetermined temperature, for example 120° C. When $T_{EXT}$ rises above the predetermined temperature, the test pack determines that the sterilization cycle has commenced. As long as $T_{EXT}$ remains above 120° C., the counter is incremented by one second at block 156. Some sterilization cycles work on one minute timers in which steam is injected for 20 seconds followed by evacuation of the chamber for 40 seconds. In such cycles, the temperature may fall below 120° C. after the first air removal pulse. The timer often cycles for up to 15 pulses. Therefore, at block 160, the test pack determines whether the temperature has been above 120° C. for over one minute, indicating that the cycle is in the sterilization hold period. If the temperature has been above 120° C. for less than one minute, the program returns to block 152. Thus, if the cycle is followed by an evacuation of the chamber, the temperature may fall below 120° C. within the minute, and block 154 will reset the counter to zero. If the counter is above one minute, however, the test pack determines that the cycle is past the pulsing stages and determines whether the counter is over three minutes and the external temperature under 50° C. If not, the test pack continues to retrieve external temperatures. Once the temperature has been over 120° C. for lover one minute and falls below 50° C. three minutes after the temperature rose above 120° C., the test pack determines that the sterilization cycle is completed and energizes the coil. Further, other types of conditions may be may be analyzed to determine if the coil should be energized, for example, if the memory is full. While some exemplary software programs have been disclosed, those skilled in the art will readily recognize that any of a number of software programs can be utilized to recognize one of the aforementioned conditions for energizing the inductive coil.

Figure 10A:
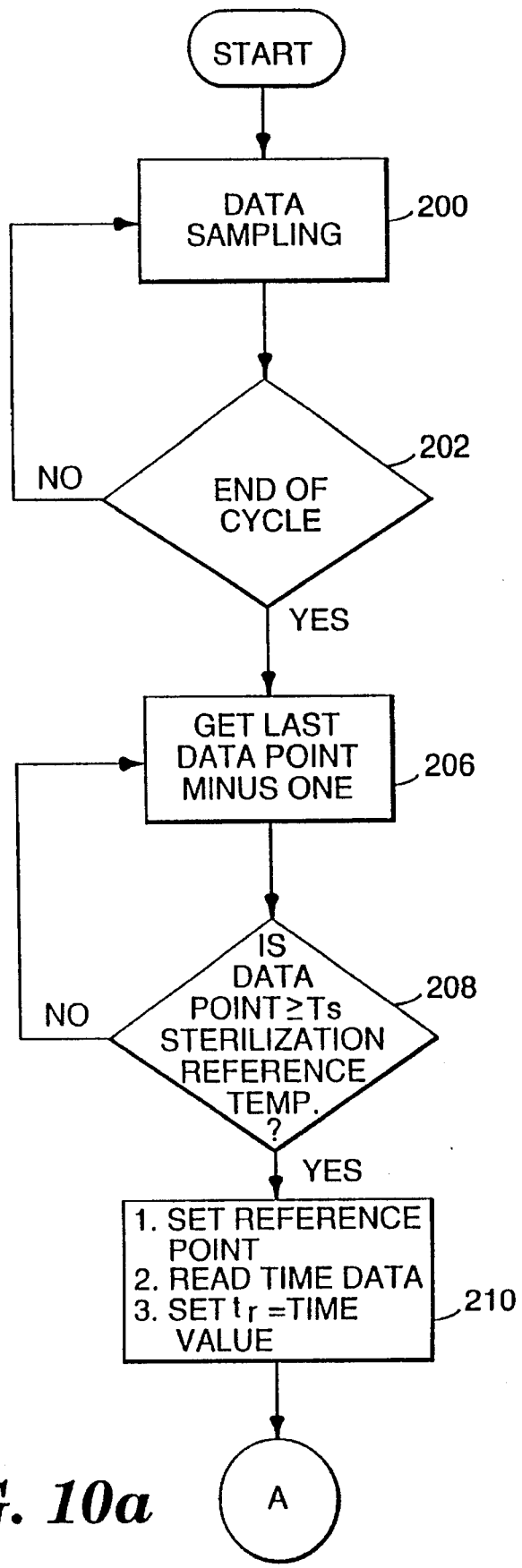
FIGS. 10A and 10B are flow diagrams for determining whether there has been a satisfactory Bowie-Dick type result.
Figure 10B:
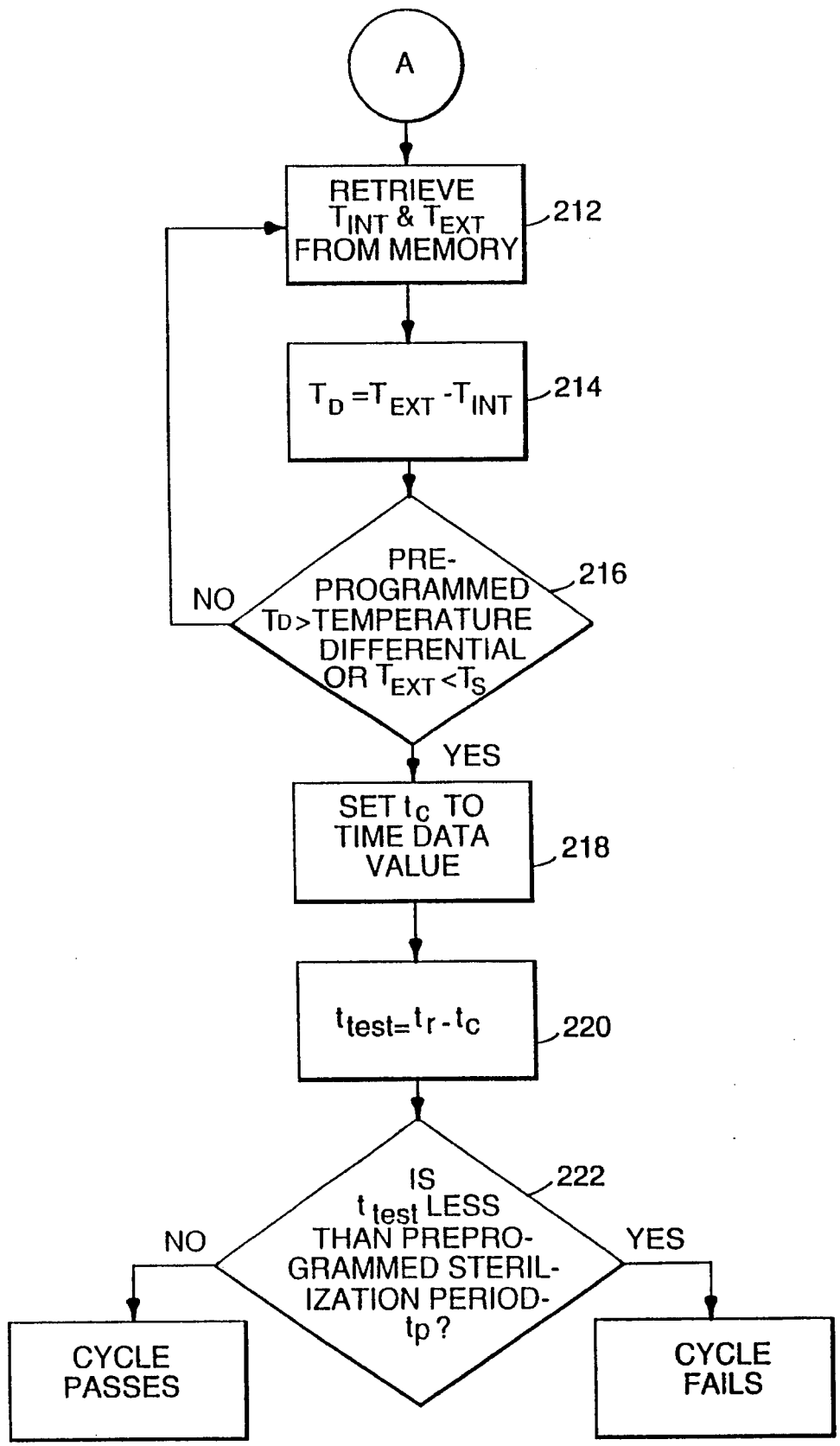

FIGS. 10A and 10B are flow diagrams of a software program used to determine whether adequate sterilant penetration has been achieved when sensing temperatures within the test pack and at the chamber reference point. For the purposes of description of the flow diagrams, a sterilization period of approximately three minutes duration will be used. If an air pocket is present, sterilant will not rapidly penetrate through the packing material. This will give rise to a temperature differential between the Sensor located within the challenge load, or at the end of the packing material, and the chamber reference sensor. The system determines if the temperature difference between the two points exceed a predetermined maximum differential at a predetermined point within the sterilization cycle. FIG. 11A shows the relationship between critical points utilized in the program. At block 200 and 202, data points are recorded from the temperature sensor within the test pack and the temperature sensor at the chamber reference point during the sterilization cycle. Also, time data corresponding to the temperature measurements is recorded. The test pack finds the end of the sterilization cycle based on the fact that at the end of the cycle, the temperature in the chamber decreases. After the chamber temperature rises above a first predefined temperature, the test pack sets a flag noting that a sterilization cycle is occurring. Once the flag is set and the chamber temperature falls below a second predefined temperature, the test pack recognizes that the sterilization cycle has ended and stops recording temperatures and time data.

After the sterilization cycle is complete, a reference point is found on the external temperature curve corresponding to the end of the sterilization phase at blocks 206 and 208. This reference point is common to every cycle and is characterized by a rapid decrease in chamber temperature. The process of finding the reference point involves scanning the external temperature data stored in memory, working backwards through the stored data. The system starts from the last data point from the external temperature curve and compares it to a preprogrammed sterilization reference temperature, $T_S$, stored in memory. In typical sterilization cycles, the temperature within the sterilization chamber continues to rise until it reaches the sterilization temperature, in many cases approximately 134° C. Once the sterilization temperature is achieved, it is held for a predetermined time, at which time the steam supply to the chamber is turned off and the temperature in the chamber falls. Thus, the sterilization reference temperature is the value representative of the sterilization hold temperature used in a particular sterilization cycle. In another embodiment, rather than preprogramming the sterilization reference temperature $T_S$, the microprocessor of the test pack can determine $T_S$ based on measurements made during the sterilization cycle to determine at which temperature the sterilizer control system used to start the cycle, thereby having a variable $T_S$. To find the reference point, the system finds the last data point from the sterilization temperature holding period. Starting from the last data point from the external temperature curve, each data point is compared to the sterilization reference temperature. If a data point is less than the sterilization reference temperature, the system compares immediately prior data points until a data point is greater than or equal to the sterilization reference temperature. The first data point that is greater than or equal to the sterilization reference temperature is assigned as the reference point and the time corresponding to the reference point is saved as reference time, $t_r$ at block 210. In FIG. 11A, reference point 250 signals the end of the sterilization phase and would approximate the sterilization reference temperature. This data point is set to be the reference point.

Once the reference point is established, the system analyzes the difference in internal temperature, the temperature at a predetermined point within the challenge load and external temperature, the temperature at the chamber reference point, searching for a critical value which indicates that satisfactory steam penetration occurred. At block 212, the system retrieves from memory both the internal and external temperatures which correspond in time. The corresponding internal and external temperatures are retrieved in reverse chronological order starting from the reference time. At block 214, a temperature difference, $T_D$, is determined for each set of internal and external temperatures, and is determined as follows:

$$T_D = T_{EXT} - T_{INT}$$

Each temperature difference $T_D$ is compared to a preprogrammed temperature differential at block 216 and the chamber temperature $T_{EXT}$ is compared to the sterilization temperature $T_S$. The preprogrammed temperature differential is the value of a temperature difference within the test pack with respect to the chamber temperature which would be considered an unsatisfactory sterilization cycle. This preprogrammed temperature differential is determined by validation experiments in which the performance of the electronic test pack is compared with that of a standard Bowie-Dick textile test pack according to recognized International, European or National standards. For example, in one embodiment, if the temperature depression is greater than 2° C. in a two minute and 40 second period after the chamber reference temperature reaches the sterilization hold temperature of 134° C., the cycle is considered unsatisfactory. Further, the chamber temperature must remain above an adequate sterilization temperature for sterilization to occur.

Once a temperature difference is greater than the preprogrammed temperature differential or the chamber temperature falls below the sterilization reference temperature, the time of that occurrence is assigned as the critical time, $t_c$ at block 218. The time at which the one of these conditions occurred is subtracted from the reference time at block 220 to determine a test period, $t_{test}$:

$$t_{test} = t_r - t_c$$

The test period, $t_{test}$, represents the period of time that the temperature within the test pack stayed within the preprogrammed temperature differential. At block 222, the test period, $t_{test}$, is compared to a preprogrammed sterilization period, $t_p$, representing the period of time which is known to ensure that every surface within the most densely packed load that a sterilizer is designed to process would be subjected to sterilant for and adequate combination of temperature and time. In the above example, $t_p$ would be two minutes 40 seconds. If the test period $t_{test}$ is greater than or equal to the preprogrammed sterilization period $t_p$, then the cycle passes. This indicates that during the test, the sterilant rapidly penetrated into the challenge pack, indicating that the level of residual air present was insufficient to prevent any load items normally processed from being subjected to sterilant for an adequate combination of time and temperature. If the test period $t_{test}$ is less than the predetermined sterilization period $t_p$, then the cycle fails. This indicates that a sufficiently large air pocket was present in the challenge pack to prevent rapid sterilant penetration.

Figure 11B:
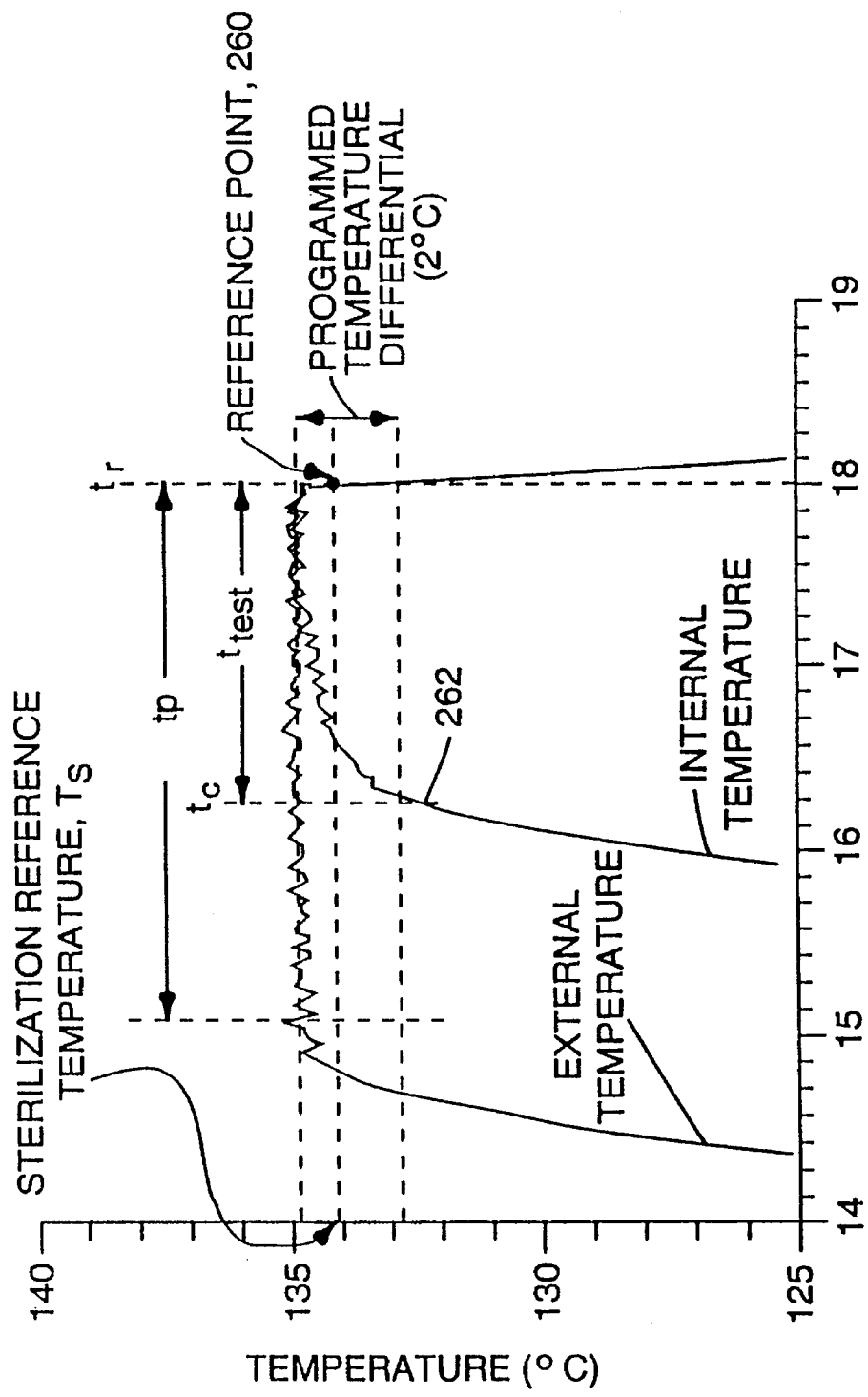

Referring to FIGS. 11A and 11B, examples of a pass cycle and a fail cycle, respectively, are shown. In a pass cycle, the test period $t_{test}$ must be greater than the period $t_p$ for the sterilization cycle to be considered adequate. In FIG. 11A, reference point 250 is established by finding the first external temperature data point, starting from the last data point and progressing in reverse chronological order, equal to the sterilization reference temperature $T_S$ of 134° C. Once reference point 250 is established, $t_r$ is set to 18 minutes, the time data corresponding to reference point 250. The sterilization cycle in FIG. 11A has a preprogrammed temperature differential of 2° C. Thus, the first point where the difference between the internal temperature and external temperature is more than 2° C., critical point 252 is determined and the critical time, $t_c$, of 15 minutes is recorded. The test period, $t_{test}$ is approximately three minutes, which is greater than the preprogrammed period, $t_p$, which is 2 minutes, 40 seconds, and the cycle passes. In FIG. 11B, reference point 260 is established and $t_r$ is set to 18 minutes. The critical time $t_c$ associated with critical point 262 is recorded. The test period $t_{test}$ is the difference between the reference time $t_r$ and the critical time $t_c$, or one minute thirty seconds. The test period is less than the preprogrammed period and thus the cycle fails.

In the embodiment of the present invention described above, two temperature measurements are used to determine whether the sterilization cycle passes. While the examination of the temperature differential between the external and internal temperatures provides direct information on the penetration of heat to the sensing point located within the challenge load, it does not directly reflect penetration of moisture to the sensing point. By inference, rapid equilibrium between the sensing point within the challenge load and the chamber indicates the absence of an insulating air pocket. It is possible, however, to directly measure the moisture penetration to the sensing point within the challenge load. In another embodiment of the present invention, a moisture sensor, such as a conductivity sensor, can be used in conjunction with a temperature sensor to determine adequate moisture penetration to the sensing point within the challenge load and therefore, by inference, steam. In this embodiment, a conductivity sensor is substituted for the temperature sensor measuring the temperature at the sensing point within the challenge load, that is, at the predetermined location challenged by the packing material. Typically, conductivity sensors consist of two inert plates having a known surface area and a known distance between them. An electrical potential difference is applied across the plates. Conductance of a current between the plates depends upon the conductivity of the medium between the plates. If the medium is moist steam, the conductivity is relatively high compared to air, which has a low conductivity. Thus, the electronic test pack can determine whether adequate steam penetration has taken place by the level of conductivity at the center of the test pack. The temperature sensor measuring the sterilization chamber temperature remains the same.

Figure 12:
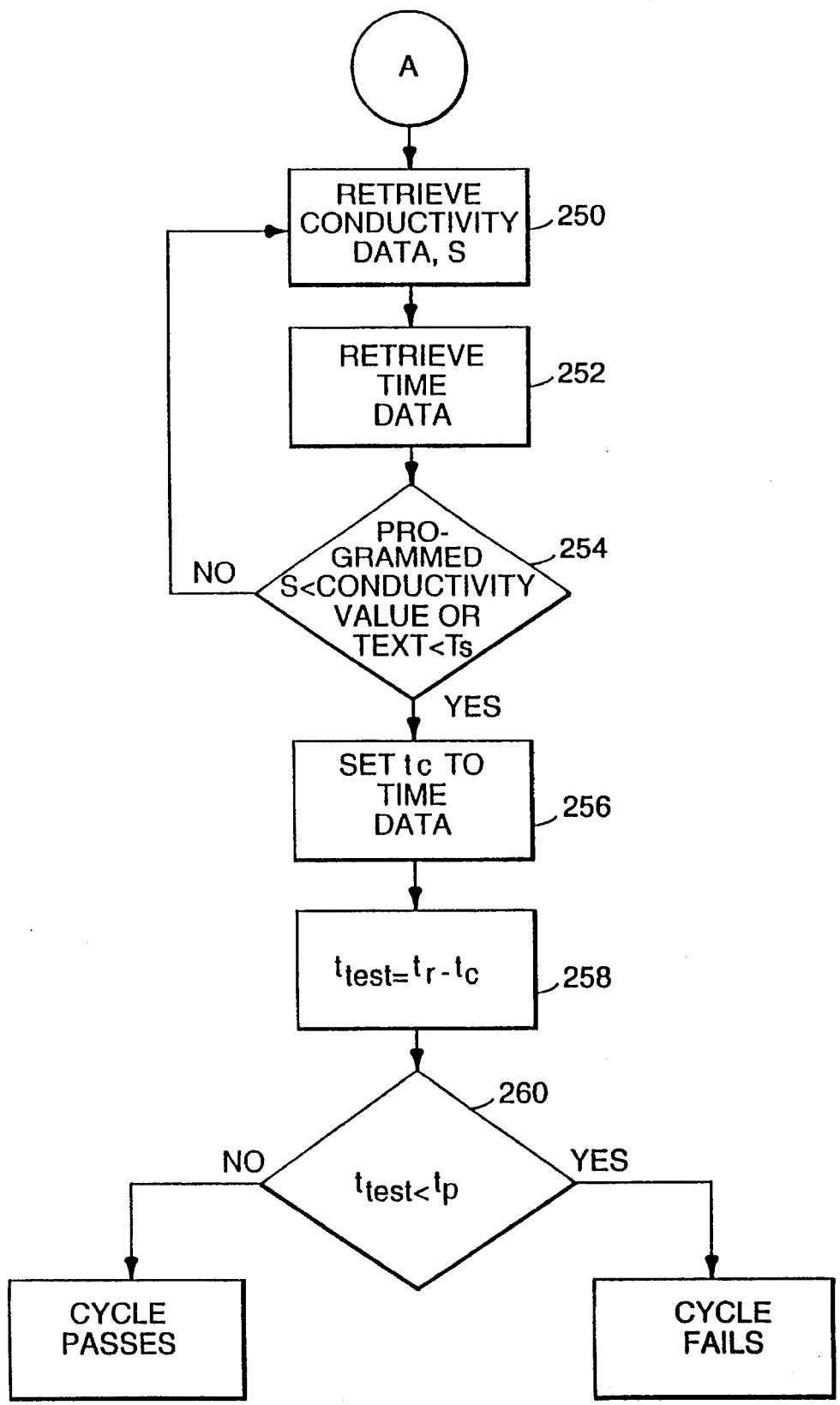
FIG. 12 is a flow diagram for determining whether there has been a satisfactory Bowie-Dick type result.

Referring to FIGS. 10A and 12, flow diagrams of a software program are shown that are used to determine if a sterilization cycle passes when conductivity is sensed by the test pack. FIG. 10A is similar to the software program when two temperature sensors are used, except rather than collecting pairs of temperature data, conductivity data and external temperature data is collected at block 200. Similarly, time data corresponding to the conductivity and temperature measurements are recorded. At blocks 206, 208 and 210, the reference point is established by analyzing the external temperature, as previously described.

Once the reference point is established, the system retrieves conductivity data, s, and its corresponding time data in reverse chronological order starting from the reference time at blocks 250 and 252. At block 254, the conductivity data is compared to a preprogrammed conductivity value and the chamber temperature is compared to the sterilization reference temperature. The preprogrammed conductivity value is a conductivity value associated with a sterilization cycle which is considered satisfactory. Once a conductivity value is less than the preprogrammed value or the chamber temperature falls below the reference temperature, the time of that occurrence is assigned as the critical time, $t_c$ at block 256. The time at which the critical conductivity value was achieved is subtracted from the reference time at block 258 to determine a test period, $t_{test}$:

$$t_{test} = t_r - t_c$$

The test period, $t_{test}$, represents the period of time that the conductivity stayed above the preprogrammed value, indicating that adequate steam penetration existed during that period. At block 260, the test period is compared to a preprogrammed sterilization period, $t_p$, determined during experimental validation, which represents the period of time that ensures that every surface within the most densely packed load which a sterilizer is designed to process, would be subjected to steam for an adequate combination of temperature and time. If $t_{test}$ is less than $t_p$, it indicates that a sufficiently large air pocket was present in the load to prevent sterilant penetration, thereby indicating a failed sterilization cycle. If $t_{test}$ is greater than or equal to $t_p$, then the cycle passes.

In yet another embodiment of the present invention, a relative humidity sensor could be used to measure moisture penetration into the pack instead of a conductivity sensor. Absolute humidity is the mass of water vapor present in a particular volume of air. The relative humidity is the ratio of the mass of water vapor present in a sample of air compared to the mass which would be present if the sample were saturated with water molecules at a defined temperature and pressure. There are a number of well known methods and apparatuses in the art which are available to measure the relative humidity of a sample of air. One well known instrument employs sensors whose electrical capacitance varies with different levels of water vapor. In one form of the instrument, the capacitance sensors consist of an aluminum and copper electrode. The surface of the aluminum is oxidized in a controlled manner so as to produce a porous surface which can absorb water molecules. The oxide layer acts as a dielectric medium whose characteristics vary depending upon the number of water molecules present. The number of water molecules absorbed in the oxide layer in turn varies according to the humidity of the surrounding medium. A sterilization cycle having a very efficient air removal stage would leave little or no residual air trapped within the challenging material of the electronic test pack. Thus, as steam entered the test pack, it would expose the capacitance humidity sensor to high concentrations of water molecules, giving a high reading rapidly after the commencement of the sterilizing stage. If, however, the air removal stage was poor, dry air would be trapped within the challenging material, thereby protecting the sensor from the advancing steam. As a result, the water molecule concentration would be low, and the sensor would give an initial low reading. As the cycle progressed, water molecules would gradually diffuse into the air pocket, causing a gradual increase in concentration which the sensor would detect.

Figure 13:
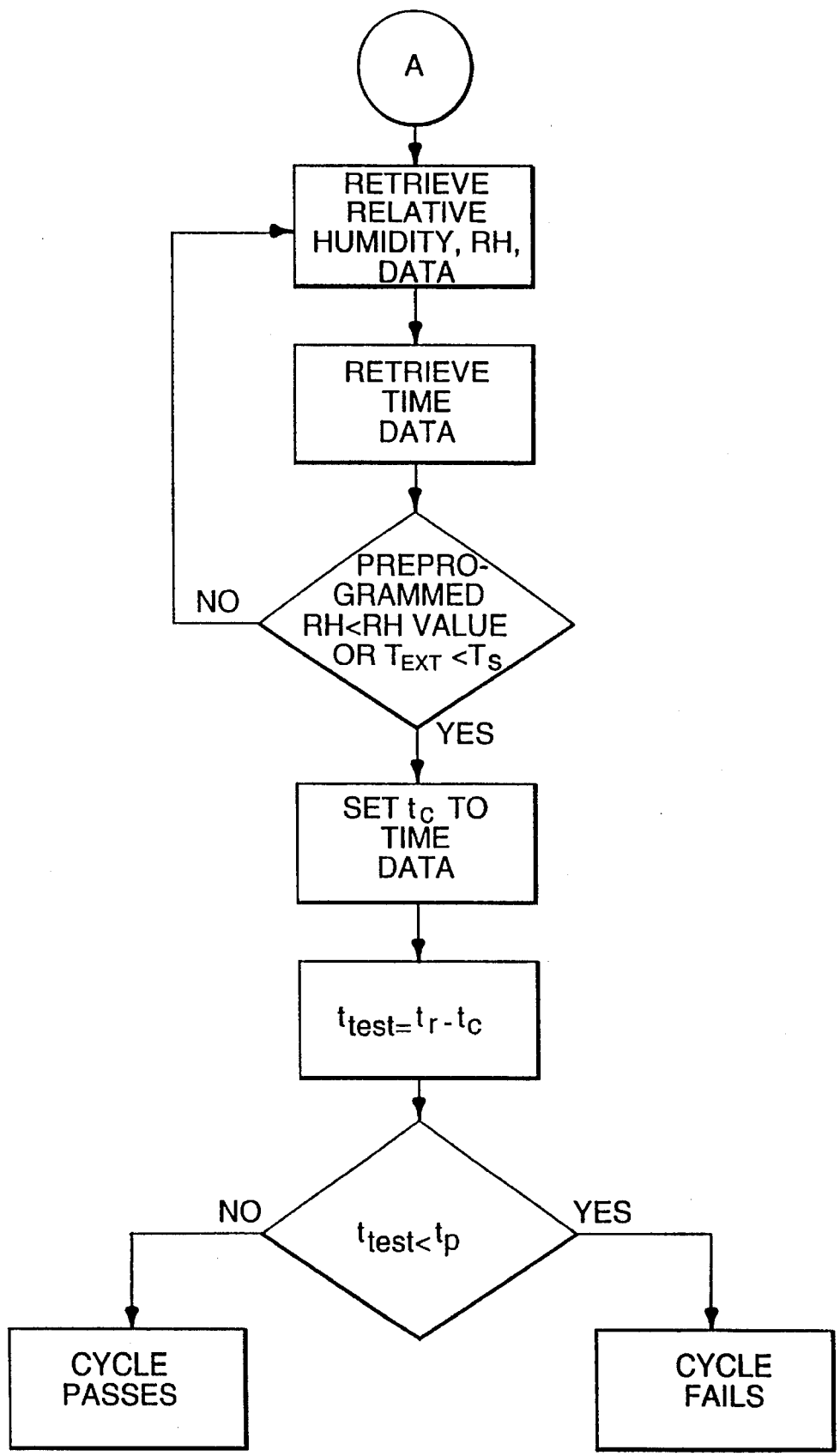
FIG. 13 is a flow diagram for determining whether there has been a satisfactory Bowie-Dick type result.

Referring to FIGS. 10A and 13, a flow diagram of a software program is shown for determining whether a sterilization cycle passes using a test pack having a capacitance humidity sensor. The flow diagram is the same as the flow diagram for the test pack having a conductivity sensor except relative humidity data is retrieved from memory and compared to a preprogrammed relative humidity value instead of conductivity data. The preprogrammed relative humidity data is a value which represents the relative humidity in saturated steam conditions at the sensing point within the challenge load.

Figure 14:
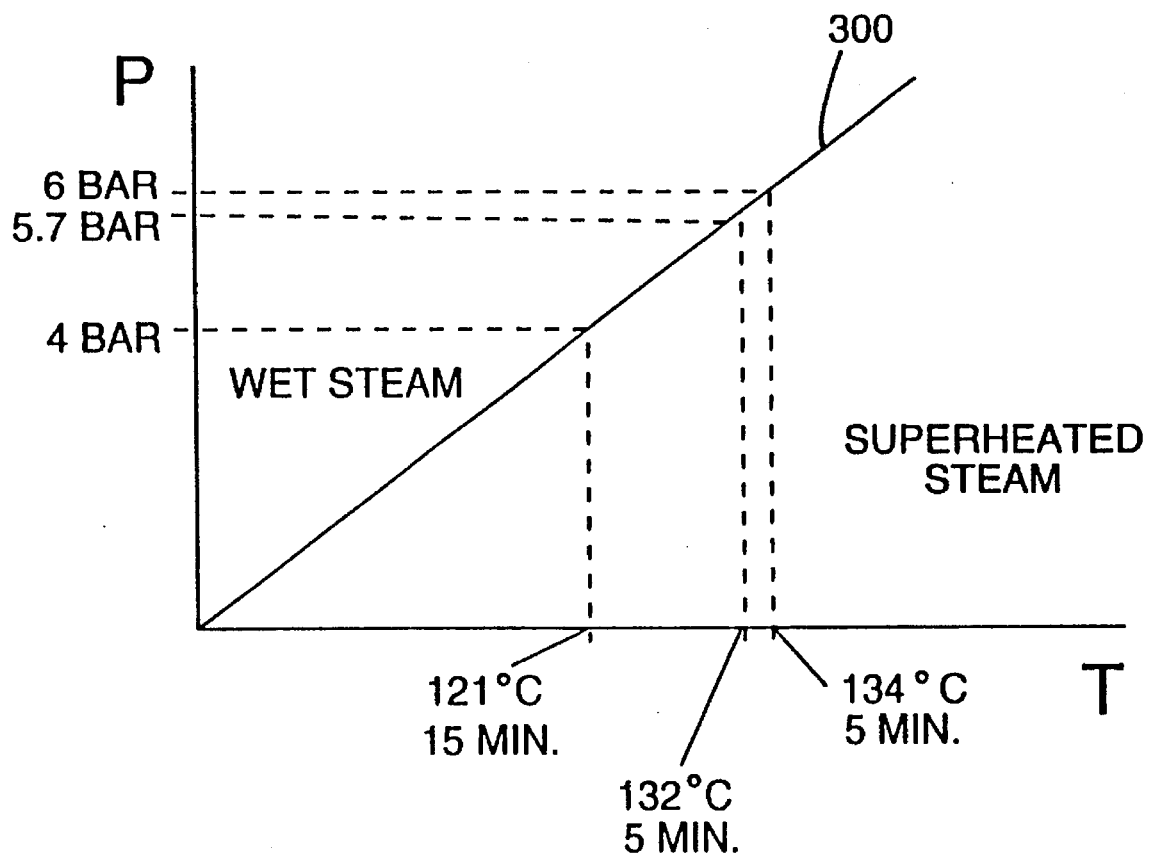
FIG. 14 is a steam phase diagram.

The aforementioned software programs all make a Bowie-Dick type determination, or in other words, whether the air removal phase of the sterilizer cycle was adequate. It is possible, however, to further determine whether the sterilization phase of the sterilizer cycle was adequate. To make this determination, it is necessary to measure not only the time and temperatures but also the steam quality within the sterilization chamber or test pack. Referring to FIG. 14, a steam phase diagram is shown. In ideal conditions, saturated steam is injected into a sterilization chamber when sterilizing a load. For saturated steam, a specific pressure-temperature relationship exists. In FIG. 14, any pressure-temperature combination that falls on line 300 indicates that the steam is saturated. For an adequate sterilization temperature, if the pressure is too high, however, wet steam exists. Similarly, for an adequate sterilization pressure, if the temperature is too low, wet steam exists. On the other hand for an adequate sterilization temperature, if the pressure is too low, superheated steam exists. Similarly, for an adequate sterilization pressure, if the temperature is too high, superheated steam exists. If wet or superheated steam is injected into the sterilization chamber, a longer sterilization time is necessary to achieve sterilization. Therefore, in an embodiment where the adequacy of the sterilization phase is determined, pressure measurements within the chamber are necessary. Further, both the air removal and the sterilization phases may be monitored.

Figure 15:
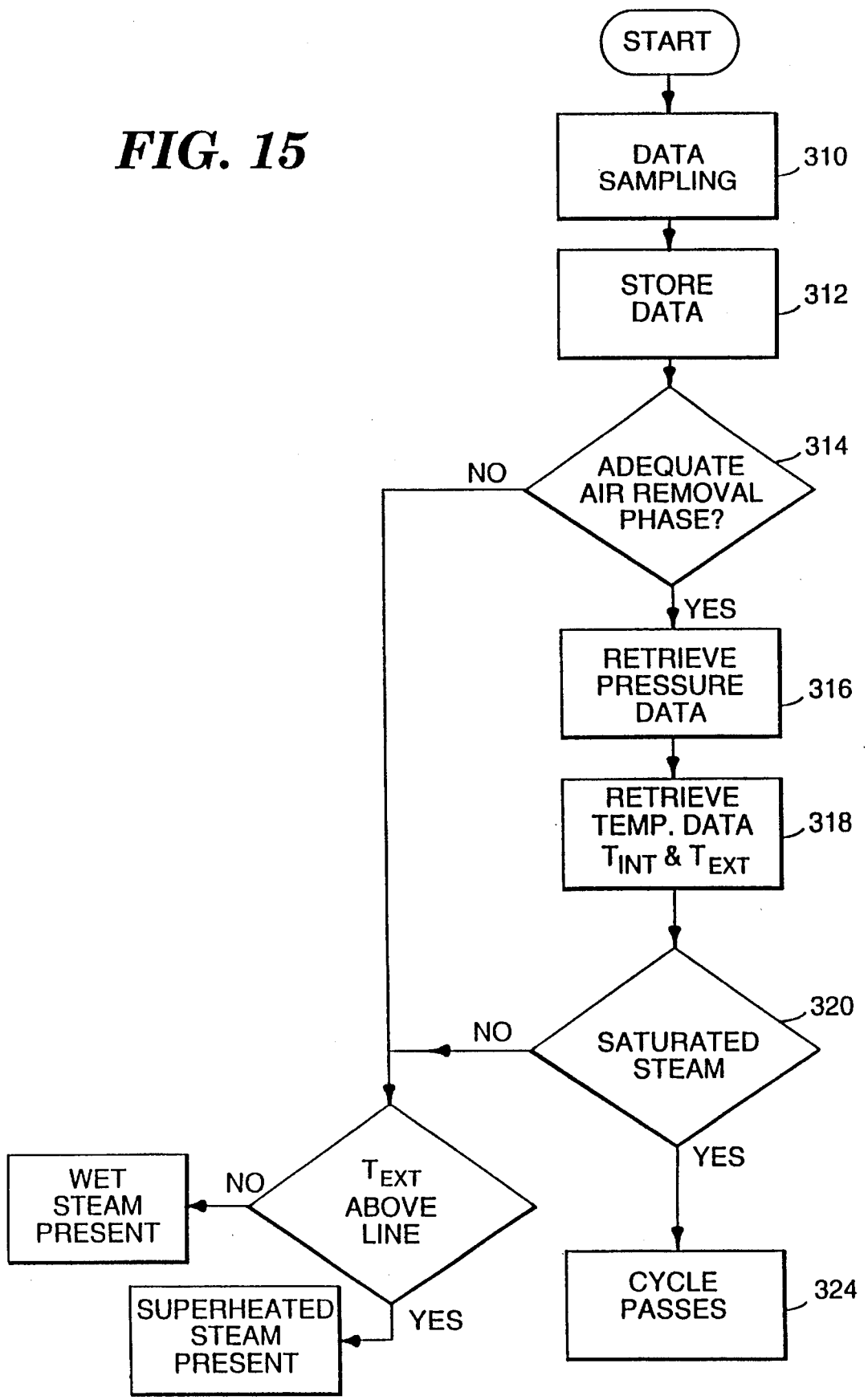
FIG. 15 is a flow diagram for determining whether there has been a satisfactory sterilization phase of the sterilization cycle.

Referring to FIG. 15, a software program for determining the efficacy of both the air removal and the sterilization phases of a sterilizer cycle is shown. At blocks 310 and 312, temperature, time and pressure data is collected and stored.

At block 314, the adequacy of the air removal phase of the cycle is analyzed. This determination can be any of the aforementioned Bowie-Dick type determinations, such as shown in FIGS. 10A, 10B, 11 and 13. If the air removal phase was not adequate, and a sufficiently large air pocket was present within the challenge load during the sterilization cycle to prevent sterilization, the quality of steam is irrelevant, and the cycle fails. If the air removal phase was adequate, however, the steam quality is analyzed to determine if the sterilization phase was satisfactory. At blocks 316 and 318, the chamber pressure and the internal and external temperatures are retrieved from memory. At block 320, the pressure and temperature data is analyzed to determine whether saturated, superheated, or wet steam was used during the sterilization phase. For example, in one embodiment, data representing a steam phase diagram could be stored in memory. If saturated steam was used, the cycle passes. If not, a cautionary signal could be provided that signaled if wet steam or superheated steam was provided as the steam source. In another embodiment, after the saturated steam determination, the length of the sterilization phase could be retrieved to determine whether conditions for sterilization were present. For example, even if superheated steam was used, if the sterilization period was sufficiently long, conditions for sterilization could still be present.

Although a preferred embodiment has been illustrated and described for the present invention, it will be appreciated by those of ordinary skill in the art that any method or apparatus which is calculated to achieve this same purpose may be substituted for the specific configurations and steps shown. For example, rather than only sensing one environmental condition at the predetermined point within challenge load of the electronic test pack, a plurality of environmental conditions could be measured. In such an embodiment, a software program could evaluate the adequacy of the sterilization cycle by looking at both the temperature differential between the center of the test pack and the chamber as well as the relative humidity at the center of the test pack. This application is intended to cover any adaptations or variations of the present invention. Therefore, it is manifestly intended that this invention be limited only by the appended claims and the equivalents thereof.

What is claimed is:

1. A sterilizer testing system for determining the efficacy of a sterilization cycle in a sterilization chamber, said system comprising:

sterilant challenging means for challenging the penetration of sterilant to a predetermined location within said sterilization chamber;

sensing means for sensing a first environmental parameter within said sterilization chamber and a second environmental parameter at said predetermined location within said sterilization chamber;

a timer;

data recording means for recording data from said sensing means and said timer; and housing means for housing at least said sensing means, said timer and said data recording means in a self-contained unit.

2. The sterilization testing system according to claim 1, wherein said sensing means comprises:

a first temperature transducer for measuring the temperature within said sterilization chamber; and a second temperature transducer for measuring the temperature at said predetermined location.

3. The sterilization testing system according to claim 1, wherein said sensing means comprises:

a plurality of temperature transducers for measuring the temperature within said sterilization chamber; and a plurality of temperature transducers for measuring the temperature at said predetermined location.

4. The sterilization testing system according to claim 1, wherein said sensing means further measures the pressure within said sterilization chamber.

5. The sterilization testing system according to claim 1, wherein said sensing means comprises:

a first temperature transducer for measuring the temperature within said sterilization chamber; and moisture sensing means for measuring the moisture at said predetermined location.

6. The sterilization testing system according to claim 5, wherein said moisture sensing means comprises a conductivity sensor.

7. The sterilization testing system according to claim 5, wherein said moisture sensing means comprises a capacitive relative humidity sensor.

8. The sterilization testing system according to claim 1, wherein said sterilant challenging means comprises:

a vertically extending container made of gas and liquid-impermeable material, said container having a top wall and sidewalls, said top wall having at least one hole therethrough for the ingress of said sterilant;

sealing means for sealing said container to said housing means; and porous packing material at least partially filling said container for defining a restricted pathway which impedes the flow of said sterilant through said container during the sterilization cycle.

9. The sterilization testing system according to claim 1, further comprising data processing means for receiving said data from said, data recording means and for analyzing said data.

10. The sterilization testing system according to claim 9, wherein said housing means further houses said data processing means.

11. The sterilization testing system according to claim 9, wherein said data processing means determines whether said sterilant adequately penetrated said sterilant challenging means to said predetermined location.

12. The sterilization testing system according to claim 11, wherein said data processing means comprises:

means for receiving said first environmental parameter from said sensing means;

means for receiving said second environmental parameter from said sensing means;

means for receiving time data from said timer corresponding to said sterilization cycle;

means for comparing said first and second environmental parameters from said sensing means and said time data from said timer with predetermined reference parameters; and means for generating a signal if said first and second environmental parameters and said time data fall within said predetermined reference parameters.

13. The sterilization testing system according to claim 11, wherein said data processing means comprises:

means for receiving first temperatures associated with said sterilization chamber from said sensing means;

means for receiving second temperatures associated with said predetermined location within said sterilization chamber from said sensing means;

means for receiving time data from said timer corresponding to said sterilization cycle;

means for funding a sterilization temperature holding period in said sterilization cycle;

means for calculating temperature differentials between said first temperatures and said second temperatures; and means for determining whether said temperature differentials were within a predetermined differential for a predetermined period during said sterilization temperature holding period.

14. The sterilization testing system according to claim 13, further comprising means for comparing said second temperatures with a predetermined sterilization temperature.

15. The sterilization testing system according to claim 13, wherein said means for determining whether said temperature differentials were within a predetermined differential for a predetermined period during said sterilization temperature holding period comprises:

means for finding a reference point, said reference point corresponding to the end of said sterilization temperature holding period;

means for comparing said temperature differentials with said predetermined differential, starting the comparison of differentials at said reference point and progressing toward the beginning of said sterilization cycle;

means for finding a critical time, said critical time occurring when said temperature differential is greater than said predetermined differential;

means for determining a test period, said test period being the period between said critical time and said end of said sterilization temperature holding period;

means for comparing said test period with said predetermined period; and means for generating a signal if said test period is greater than or equal to said predetermined period.

16. The sterilization testing system according to claim 11, wherein said data processing means comprises:

means for receiving first temperatures associated with said sterilization chamber from said sensing means;

means for receiving second temperatures associated with said predetermined location within said sterilization chamber from said sensing means;

means for receiving time data from said timer corresponding to said sterilization cycle;

means for finding a sterilization temperature holding period in said sterilization cycle;

means for calculating temperature differentials between said first temperatures and said second temperatures; and means for determining whether said temperature differential was within a predetermined differential at a predetermined point associated with the beginning of said sterilization temperature holding period.

17. The sterilization testing system according to claim 11, wherein a first light emitting diode emits light if said data processing means determines said sterilant adequately penetrated said sterilant challenging means and a second light emitting diode emits light if said data processing means determines said sterilant did not adequately penetrate said sterilant challenging means.

18. The sterilization testing system according to claim 1, further comprising:

data transfer means for transferring said data from said data recording means; and data receiving means for receiving data from said data transfer means, said data receiving means located at a location remote from said data transfer means.

19. The sterilization testing system according to claim 18, further comprising:

a power supply;

a magnetically actuated switching device positioned such that when said sterilization testing system is placed in proximity to a magnet, said magnet actuates said switching device to a first position to turn on said power supply;

a coil located proximate to said magnetically actuated switching device for emitting a magnetic field to switch said switching device to a second position to turn off said power supply; and means for energizing said inductive coil when data transfer from said data transfer means to said data receiving means is complete.

20. The sterilization testing system according to claim 18, wherein said data transfer means optically transfers said data.

21. The sterilization testing system according to claim 20, wherein said data transfer means comprises a light emitting diode for optical transmission of said data.

22. The sterilization testing system according to claim 21, wherein said housing means houses said light emitting diode, said housing means having a transparent portion.

23. The sterilization testing system according to claim 18, wherein said data transfer means comprises an RF generator for generating RF signals representing said data.

24. The sterilization testing system according to claim 18, wherein said housing means houses said data transfer means.

25. The sterilization testing system according to claim 18, wherein said data receiving means includes an actuating device and wherein said sterilization testing system further comprises a proximity actuated switching device positioned such that when said sterilization testing system is placed in proximity to said data receiving means, said actuating device actuates said switching device to signal said data transfer means to transfer data.

26. The sterilization testing system according to claim 25, wherein said data receiving means is configured to receive said housing means in a predetermined orientation, said predetermined orientation based on the locations of said actuating device and said proximity actuated switching device.

27. The sterilization testing system according to claim 18, wherein said data receiving means further comprises interface means for interfacing to external devices.

28. The sterilization testing system according to claim 18, wherein said data receiving means further comprises data processing means for determining whether said sterilant adequately penetrated said sterilant challenging means to said predetermined location.

29. The sterilization testing system according to claim 1, further comprising:

a power supply; and a proximity actuated switching device positioned such that when said sterilization testing system is placed in proximity to an actuating device, said actuating device actuates said switching device to a first position to turn on said power supply.

30. The sterilization testing system according to claim 29, further comprising means for switching said switching device to a second position to turn off said power supply when said sterilization cycle is complete.

31. The sterilization testing system according to claim 29, further comprising means for switching said switching device to a second position to turn off said power supply when said system has not been placed within said sterilization chamber.

32. The sterilization testing system according to claim 1, wherein said housing means includes a vacuum inside said housing means.

33. The sterilization testing system according to claim 1, further comprising a one-way valve positioned in said housing means, said one-way valve opening when pressure external to said housing means is lower then pressure within said housing means.

34. The sterilization testing system according to claim 1, wherein said sterilant challenging means is sealably connected to said housing means around said predetermined location.

35. The sterilization testing system according to claim 1, wherein said sensing means comprises:

a cap, said cap protruding from said housing means to said predetermined location;

a first sensor for sensing a first environmental condition; and a second sensor for sensing a second environmental condition.

36. The sterilization testing system according to claim 35, wherein said sterilant challenging means is sealably connected to said housing means and comprises a spherical challenging medium centered at said predetermined location.

37. A self-contained sterilizer testing system for determining the efficacy of a sterilization cycle in a sterilization chamber, said system comprising:

sterilant challenging means for challenging the penetration of sterilant to a predetermined location within said sterilization chamber;

a first environmental sensor for sensing a first environmental parameter within said sterilization chamber;

a second environmental sensor for sensing a second environmental parameter at said predetermined location within said sterilization chamber;

a timer;

means for receiving said first environmental parameter from said first environmental sensor;

means for receiving said second environmental parameter from said second environmental sensor;

means for receiving time data from said timer corresponding to said sterilization cycle;

means for comparing said first and second environmental parameters from said first and second environmental sensors and said time data from said timer with predetermined reference parameters;

a first light emitting diode, said first light emitting diode emitting light if said first and second environmental parameters and said time data fall within said predetermined reference parameters;

a second light emitting diode, said second light emitting diode emitting light if any of said first and second environmental parameters and said time data fall outside said predetermined reference parameters; and housing means for housing said sterilization challenging means, said first and second environmental sensors, said timer, said means for receiving said first and second environmental parameters from said first and second environmental sensors, said means for receiving time data, said means for comparing said first and second environmental parameters and said first and second light emitting diodes in a self-contained unit.

38. A sterilizer testing system for determining the efficacy of a sterilization cycle in a sterilization chamber, said system comprising:

sterilant challenging means for challenging the penetration of sterilant to a predetermined location within said sterilization chamber;

sensing means for sensing a first environmental parameter within said sterilization chamber and a second environmental parameter at said predetermined location within said sterilization chamber;

steam quality determination means for determining the quality of steam used in said sterilization cycle;

a timer;

data recording means for recording data from said sensing means and said timer; and housing means for housing at least said sensing means, said steam quality determination means, said timer and said data recording means in a self-contained unit.

39. The sterilization testing system according to claim 38, wherein said first and second environmental parameters are first and second temperatures and wherein said steam quality determination means comprises:

a pressure sensor for measuring the pressure within said sterilization chamber; and processing means for processing said first and second temperatures and said pressure to determine said steam quality.

40. A method of determining the efficacy of a sterilization cycle in a sterilization chamber using a self-contained electronic test pack, said test pack comprising a first sensor and a second sensor for sensing environmental parameters, a timer, a memory, and a data processor, said method comprising the steps of:

challenging the penetration of sterilant to said first sensor;

sensing a first environmental parameter with said first sensor;

sensing a second environmental parameter within said sterilization chamber with said second sensor;

recording to memory time data from said timer corresponding to said first and second environmental parameters;

comparing with said data processor said first and second environmental parameters and said time data with predetermined reference parameters stored in memory; and generating a signal from said data processor if said first and second environmental parameters and said time data fall within said predetermined reference parameters.

41. The method of determining the efficacy of a sterilization cycle in a sterilization chamber according to claim 40, wherein said first environmental parameter is a first temperature and said second environmental parameter is a second temperature.

42. The method of determining the efficacy of a sterilization cycle in a sterilization chamber according to claim 41, wherein said predetermined reference parameters comprise a threshold temperature, a predetermined temperature differential and a predetermined period.

43. The method of determining the efficacy of a sterilization cycle in a sterilization chamber according to claim 40, wherein said first environmental parameter is temperature and said second environmental parameter is conductivity.

44. The method of determining the efficacy of a sterilization cycle in a sterilization chamber according to claim 43, wherein said predetermined reference parameters comprise a threshold temperature, a predetermined conductance and a predetermined period.

45. The method of determining the efficacy of a sterilization cycle in a sterilization chamber according to claim 40, wherein said first environmental parameter is temperature and said second environmental parameter is relative humidity.

46. The method of determining the efficacy of a sterilization cycle in a sterilization chamber according to claim 45, wherein said predetermined reference parameters comprise a threshold temperature, a predetermined relative humidity, and a predetermined period.

47. A method of determining the efficacy of a sterilization cycle in a sterilization chamber using a self-contained electronic test pack, said test pack comprising a first temperature transducer and a second temperature transducer, a timer, a memory and a data processor, said method comprising the steps of:

challenging the penetration of sterilant to said first temperature transducer;

sensing a first temperature with said first temperature transducer;

sensing a second temperature within said sterilization chamber with said second temperature transducer;

recording to memory time data corresponding to said first and second temperatures;

finding with said data processor a sterilization temperature holding period in said sterilization cycle;

calculating with said data processor temperature differentials between said first temperatures and said second temperatures; and generating a signal from said data processor if said temperature differentials were within a predetermined differential for a predetermined period during said sterilization temperature holding period.

48. The method of determining the efficacy of a sterilization cycle in a sterilization chamber according to claim 47, wherein said step of generating a signal if said temperature differentials were within a predetermined differential for a predetermined period during said sterilization temperature holding period comprises the data processor implemented steps of:

finding a reference point, said reference point corresponding to the end of said sterilization temperature holding period;

comparing said temperature differentials with said predetermined differential, starting the comparison of differentials at said reference point and progressing toward the beginning of said sterilization cycle;

finding a critical time, said critical time occurring when said temperature differential is greater than said predetermined differential;

determining a test period, said test period being the period between said critical time and said end of said sterilization temperature holding period;

comparing said test period with said predetermined period; and generating a pass signal if said test period is greater than or equal to said predetermined period.

49. A method of determining the efficacy of a sterilization cycle in a sterilization chamber using a self-contained electronic test pack, said test pack comprising a first sensor and a second sensor for sensing environmental parameters, a timer, a memory and a data processor, said method comprising the steps of:

challenging the penetration of steam to said first sensor;

sensing a first environmental parameter with said first sensor;

sensing a second environmental parameter within said sterilization chamber with said second sensor;

determining steam quality of said steam;

recording to said memory time data corresponding to said first and second environmental parameters;

comparing with said data processor said first and second environmental parameters, steam quality and said time data with predetermined reference parameters; and generating a signal from said data processor if said first and second environmental parameters, steam quality and said time data fall within said predetermined reference parameters.

50. The method of determining the efficacy of a sterilization cycle in a sterilization chamber according to claim 49, wherein said test pack further comprises a pressure sensor and wherein said first and second environmental parameters are a first and second temperature, said step of determining steam quality comprises the steps of:

sensing pressure in said sterilization chamber with said pressure sensor; and comparing said pressure and said first and second temperatures with parameters of a steam phase diagram stored in said memory.

51. A self-contained unit which can be located within a sterilization chamber for testing the efficacy of a sterilization cycle, the unit comprising:

a sterilant challenging path for challenging the penetration of sterilant from outside the unit to a predetermined location within the unit;

electronic means operable, during said sterilization cycle, to determine whether or not sterilant has penetrated adequately to said predetermined location; and housing means for housing said sterilant challenging path and said electronic means, thereby forming said self-contained unit.

52. The self-contained unit according to claim 51, wherein said electronic means is further operable to provide an indication of whether or not sterilant has penetrated adequately to said predetermined location.

53. The self-contained unit according to claim 52, wherein said electronic means provides said indication from within said sterilization chamber.

54. The self-contained unit according to claim 51, wherein said electronic means comprises:

sensing means for sensing a first environmental parameter within said sterilization chamber and a second environmental parameter at said predetermined location within said sterilization chamber;

a timer; and data recording means for recording data from said sensing means and said timer.

55. The self-contained unit according to claim 54, wherein said electronic means further comprises:

means for receiving said first environmental parameter from said sensing means;

means for receiving said second environmental parameter from said sensing means;

means for receiving time data from said timer corresponding to said sterilization cycle;

means for comparing said first and second environmental parameters from said sensing means and said time data from said timer with predetermined reference parameters; and means for generating a signal if said first and second environmental parameters and said time data fall within said predetermined reference parameters.

56. The self-contained unit according to claim 54, wherein said electronic means further comprises:

means for receiving first temperatures associated with said sterilization chamber from said sensing means;

means for receiving second temperatures associated with said predetermined location within said sterilization chamber from said sensing means;

means for receiving time data from said timer corresponding to said sterilization cycle;

means for finding a sterilization temperature holding period in said sterilization cycle;

means for calculating temperature differentials between said first temperatures and said second temperatures; and means for determining whether said temperature differentials were within a predetermined differential for a predetermined period during said sterilization temperature holding period.

57. The self-contained unit according to claims 56, further comprising means for comparing said second temperatures with a predetermined sterilization temperature.

58. The self-contained unit according to claim 56, wherein said means for determining whether said temperature differentials were within a predetermined differential for a predetermined period during said sterilization temperature holding period comprises:

means for finding a reference point, said reference point corresponding to the end of said sterilization temperature holding period;

means for comparing said temperature differentials with said predetermined differential, starting the comparison of differentials at said reference point and progressing toward the beginning of said sterilization cycle;

means for finding a critical time, said critical time occurring when said temperature differential is greater than said predetermined differential;

means for determining a test period, said test period being the period between said critical time and said end of said sterilization temperature holding period;

means for comparing said test period with said predetermined period; and means for generating a signal if said test period is greater than or equal to said predetermined period.

59. The self-contained unit according to claim 54, wherein said electronic means further comprises:

means for receiving first temperatures associated with said sterilization chamber from said sensing means;

means for receiving second temperatures associated with said predetermined location within said sterilization chamber from said sensing means;

means for receiving time data from said timer corresponding to said sterilization cycle;

means for finding a sterilization temperature holding period in said sterilization cycle;

means for calculating temperature differentials between said first temperatures and said second temperatures; and means for determining whether said temperature differential was within a predetermined differential at a predetermined point associated with the beginning of said sterilization temperature holding period.

60. The self-contained unit according to claim 51, wherein said electronic means further comprises:

a first temperature transducer for measuring the temperature within said sterilization chamber; and a second temperature transducer for measuring the temperature at said predetermined location.

61. The self-contained unit according to claim 51, wherein said electronic means further comprises:

a plurality of temperature transducers for measuring the temperature within said sterilization chamber; and a plurality of temperature transducers for measuring the temperature at said predetermined location.

62. The self-contained unit according to claim 51, wherein said electronic means further measures the pressure within said sterilization chamber.

63. The self-contained unit according to claim 51, wherein said electronic means further comprises:

a first temperature transducer for measuring the temperature within said sterilization chamber; and moisture sensing means for measuring the moisture at said predetermined location.

64. The self-contained unit according to claim 63, wherein said moisture sensing means comprises a conductivity sensor.

65. The self-contained unit according to claim 63, wherein said moisture sensing means comprises a captive relative humidity sensor.

66. The self-contained unit according to claim 51, further comprising:

data recording means for recording data; and data transfer means for transferring said data from said data recording means to data receiving means for receiving data from said data transfer means, said data receiving means located at a location remote from said data transfer means.

67. The self-contained unit according to claim 66, wherein said data transfer means optically transfers said data.

68. The self-contained unit according to claim 67, wherein said data transfer means comprises a light emitting diode for optical transmission of said data.

69. The self-contained unit according to claim 66, wherein said data transfer means comprises an RF generator for generating RF signals representing said data.

\* \* \* \* \*

UNITED STATES PATENT AND TRADEMARK OFFICE
CERTIFICATE OF CORRECTION

PATENT NO.: 5,565,634            Page 1 of 2

DATED: October 15, 1996

INVENTOR(S): Josef A. Graessle, Steven S. Kirckof, Brian Kirk, Werner R. Schwarz, Theo N. Wildt It is certified that error appears in the above-identified patent and that said Letters Patent is hereby corrected as shown below:

Title page,
    in the Title, please delete "STERLIZERS" and insert therefore --STERILIZERS--.

Item [56] References Cited, Foreign Patent Documents, delete "028245" and insert therefore --0428245--.

Column 1, line 22, insert --,-- after the word "time".

Column 1, line 58, delete the first occurrence of the word "for".

Column 2, line 48, insert --a-- after the word "for".

Column 2, line 62, delete "In".

Column 3, line 13, delete "so" and insert therefore --to--.

Column 4, line 42, delete "diagrams" and insert therefore --diagram--.

Column 5, line 2, delete "deter mining" and insert therefore --determining--.

Column 5, line 32, delete the first occurrence of the word "is".

Column 5, line 41, delete "Wall" and insert therefore --wall--.

Column 6, line 27, delete "includes" and insert therefore --include--.

UNITED STATES PATENT AND TRADEMARK OFFICE
CERTIFICATE OF CORRECTION

PATENT NO.: 5,565,634

DATED: October 15, 1996

INVENTOR(S): Josef A. Graessle, Steven S. Kirckof, Brian Kirk, Werner R. Schwarz, Theo N. Wildt It is certified that error appears in the above-identified patent and that said Letters Patent is hereby corrected as shown below:

Column 7, line 38, delete "A: and insert therefore --An--.

Column 12, line 19, delete "lover" and insert therefore --over--.

Column 12, line 22, delete "may be".

Column 12, line 37, delete "Sensor" and insert therefore --sensor--.

Column 13, line 44, the equation should read --$T_D = T_{EXT} - T_{INT}$--.

Column 18, line 34, delete "," after the word "said".

Column 19, line 1, delete "funding" and insert therefore --finding--.

Signed and Sealed this

Ninth Day of December, 1997

Attest:

Attesting Officer

BRUCE LEHMAN

Commissioner of Patents and Trademarks